United States Patent
Faull et al.

(10) Patent No.: US 7,572,826 B2
(45) Date of Patent: Aug. 11, 2009

(54) THIOPHENE-CARBOXAMIDE DERIVATIVES AND THEIR USE AS INHIBITORS OF THE ENZYME IKK-2

(75) Inventors: Alan Wellington Faull, Macclesfield (GB); Craig Johnstone, Macclesfield (GB); Andrew David Morley, Macclesfield (GB); Jeffrey Philip Poyser, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 112 days.

(21) Appl. No.: 10/542,326

(22) PCT Filed: Jan. 13, 2004

(86) PCT No.: PCT/GB2004/000096

§ 371 (c)(1),
(2), (4) Date: Jul. 13, 2005

(87) PCT Pub. No.: WO2004/063186

PCT Pub. Date: Jul. 29, 2004

(65) Prior Publication Data

US 2006/0058522 A1    Mar. 16, 2006

(30) Foreign Application Priority Data

Jan. 15, 2003    (SE) .................. 0300092

(51) Int. Cl.
*A61K 31/381* (2006.01)
*C07D 333/36* (2006.01)

(52) U.S. Cl. .................. 514/447; 514/448; 549/63; 549/64; 549/69

(58) Field of Classification Search .......... 549/63, 549/64, 69; 514/447, 448
See application file for complete search history.

(56) References Cited

U.S. PATENT DOCUMENTS

| | | | |
|---|---|---|---|
| 3,963,750 A | 6/1976 | Goudie | |
| 5,258,357 A | 11/1993 | Muenster et al. | |
| 5,571,810 A | 11/1996 | Matsuo et al. | |
| 5,679,670 A | 10/1997 | Dean et al. | |
| 6,048,880 A | 4/2000 | Kawai et al. | |
| 6,380,214 B1 | 4/2002 | Gant et al. | |
| 6,414,013 B1 | 7/2002 | Fancelli et al. | |
| 6,699,854 B2 | 3/2004 | Wang et al. | |
| 6,809,088 B2 | 10/2004 | Chabrier de Lassauniere et al. | |
| 6,835,745 B2 | 12/2004 | Coghlan et al. | |
| 6,875,790 B2 | 4/2005 | Bertenshaw et al. | |
| 6,881,735 B2 | 4/2005 | Schindler et al. | |
| 6,881,741 B2 | 4/2005 | Kong et al. | |
| 7,019,027 B2 | 3/2006 | Linden et al. | |
| 7,084,170 B2 | 8/2006 | Grossman et al. | |
| 7,084,171 B2 | 8/2006 | Grainger et al. | |
| 7,098,240 B2 | 8/2006 | Griffiths et al. | |
| 7,125,896 B2 | 10/2006 | Faull et al. | |
| 7,166,639 B2 | 1/2007 | Wan et al. | |
| 7,196,106 B2 | 3/2007 | Duffy et al. | |
| 7,358,376 B2 * | 4/2008 | Baxter et al. .................. 549/69 |
| 2006/0058522 A1 | 3/2006 | Faull et al. | |
| 2006/0111431 A1 | 5/2006 | Morley et al. | |
| 2007/0015819 A1 | 1/2007 | Faull et al. | |

FOREIGN PATENT DOCUMENTS

| | | |
|---|---|---|
| EP | 0202538 | 11/1986 |
| EP | 0853083 | 7/1998 |
| EP | 0908456 | 4/1999 |
| GB | 1468012 | 3/1977 |
| GB | 2195634 | 4/1988 |
| WO | WO 98/02430 | 1/1998 |
| WO | WO 98/54116 | 12/1998 |
| WO | WO 99/46244 | 9/1999 |
| WO | WO 00/71532 | 11/2000 |
| WO | WO 01/58890 | 8/2001 |
| WO | WO 01/98290 | 12/2001 |
| WO | WO 02/30353 | 4/2002 |
| WO | WO 02/46171 | 6/2002 |
| WO | WO 03/010158 | 2/2003 |
| WO | WO 03/010163 | 2/2003 |
| WO | WO 03/028731 | 4/2003 |
| WO | WO 03/029241 | 4/2003 |
| WO | WO 2004/063185 | 7/2004 |
| WO | WO 2004/063186 | 7/2004 |

OTHER PUBLICATIONS

U.S. Appl. No. 09/868,884, filed Feb. 5, 2002, to Baxter, et al.*
Karen, M. et al. "NF-kB in cancer: from innocent bystander to major culprit," *Nat. Rev. Cancer*, 2: 301-310 (2002).
Luo et al., "IKK/NF-kB signaling: balancing life and death—a new approach to cancer therapy," *J. of Clin. Inv.*, 115:10: 2625 (2005).

(Continued)

*Primary Examiner*—Joseph K McKane
*Assistant Examiner*—Janet L Coppins
(74) *Attorney, Agent, or Firm*—Fish & Richardson P.C.

(57) ABSTRACT

The invention relates to thiophene carboxamides of formula (I), wherein A, $R^1$, $R^2$, $R^3$, $R^4$, $R^5$ and X are as defined in the specification, processes and intermediates used in their preparation, pharmaceutical compositions containing them and their use in therapy.

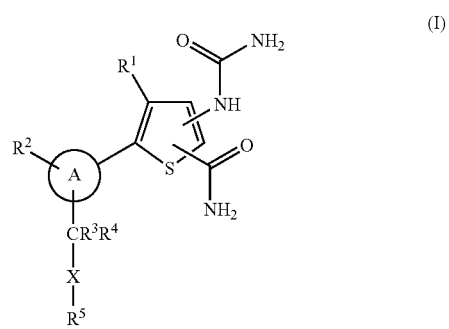

16 Claims, No Drawings

OTHER PUBLICATIONS

Orlowski, et al., "NF-kB as a therapeutic target in cancer," *Trends in Mol. Med.*, 8:8: 385 (2002).

Awada et al., "The pipeline of new anticancer agents for breast cancer treatment in 2003", *Critical Rewiews in Oncology/Hematology* 48:45-63 (2003).

Berkow et al., The Merck Manual of Diagnosis and Therapy, 16th Edition, © 1992, Merck Research Laboratories, Rahway, NJ, pp. 1488 and 2664.

Chen et al., "TNF-R1 Signaling: A Beautiful Pathway", *Science* 296:1634-1635 (2002).

Compston et al., "Multiple sclerosis", *The Lancet* 359:1221-1231 (2002).

Du et al., "Aryl ureas represent a new class of anti-trypansomal agents", *Chemistry & Biology* 7:733-742 (2000).

Goluh et al., "Molecular Classification of Cancer: Class Discovery and Class Predicition by Gene Expression Monitoring", *Science* 286:531-537 (1999).

Gripenberg, "Common serological features in rheumatoid arthritis and yersinia arthritis", *Scand. J. Rheumatology* 10:85-91 (1981).

Hartung et al., "What do we know about the mechanism of action of disease-modifying treatments in MS?" *J Neurol* 251(Suppl. 5):V/12-V/29 (2004).

Lala et al., "Role of nitric oxide in tumor progression: Lessons from experimental tumors", *Cancer and Metastasis Reviews* 17:91-106 (1998).

Parrish et al., "Preparation of 2-ureidothiophenes as angiogenesis and Chk1 kinase inhibitors for treating various forms of cancer and hyperproliferative disorders", CAPLUS 138:304153, 2003.

Zayed et al., "Studies on 5-aminopyrazole derivatives. Synthesis of some new fused pyrazole derivatives", *Monatsh. Chem.* 115:431-436 (1984).

Cancer [online], [retrieved on Jul. 6, 2007] Retrieved from the Internet, URL; http://www.nlm.nih.gov/medlineplus/cancer.html.

Cancer [online], [retrieved on Jul. 6, 2007] Retreived from the Internet, URL; http://en.wikipedia.org/wiki/Cancer.

Diabetes Guide [online], [retreived from the internet on Jun. 17, 2008] [URL; http://www.diabetes.webmd.com/guide/diabetes-overview].

* cited by examiner

THIOPHENE-CARBOXAMIDE DERIVATIVES AND THEIR USE AS INHIBITORS OF THE ENZYME IKK-2

CROSS-REFERENCE TO RELATED APPLICATIONS

This application is the National Stage of International Application No. PCT/GB2004/000096, filed Jan.13, 2004, which claims the benefit of Swedish Patent application Ser. No. 0300092-4, filed Jan.15, 2003. The contents of both prior applications are hereby incorporated by reference in their entireties.

FIELD OF THE INVENTION

The present invention relates to thiophene carboxamide derivatives, processes and intermediates used in their preparation, pharmaceutical compositions containing them and their use in therapy.

BACKGROUND OF THE INVENTION

The NF-κB (nuclear factor κB) family is composed of homo- and heterodimers of the Rel family of transcription factors. A key role of these transcription factors is to induce and co-ordinate the expression of a broad spectrum of pro-inflammatory genes including cytokines, chemokines, interferons, MHC proteins, growth factors and cell adhesion molecules (for reviews see Verma et. al., Genes Dev. 9:2723-35, 1995; Siebenlist et. al., Ann. Rev. Cell. Biol. 10:405-455, 1994; Bauerle and Henkel, Ann. Rev. Immunol., 12:141-179, 1994; Barnes and Karin, New Engl. J. Med., 336:1066-1071, 1997).

The most commonly found Rel family dimer complex is composed of p50 NFkB and p65 RelA (Baeuerle and Baltimore, Cell 53:211-217, 1988; Baeuerle and Baltimore, Genes Dev. 3:1689-1698, 1989). Under resting conditions NF-κB dimers are retained in the cytoplasm by a member of the IκB family of inhibitory proteins (Beg et. al., Genes Dev., 7:2064-2070, 1993; Gillnore and Morin, Trends Genet. 9:427-433, 1993; Haskil et. al., Cell 65:1281-1289, 1991). However, upon cell activation by a variety of cytokines or other external stimuli, IκB proteins become phosphorylated on two critical serine residues (Traenckner et. al., EMBO J., 14:2876, 1995) and are then targeted for ubiquitination and proteosome-mediated degradation (Chen, Z. J. et. al., Genes and Dev. 9:1586-1597, 1995; Scherer, D.C. et. al., Proc. Natl. Acad. Sci. USA 92:11259-11263, 1996; Alkalay, I. et. al., Proc. Natl. Acad. Sci. USA 92:10599-10603, 1995). The released NF-κB is then able to translocate to the nucleus and activate gene transcription (Beg et. al., Genes Dev., 6:1899-1913,1992).

A wide range of external stimuli have been shown to be capable of activating NF-κB (Baeuerle, P. A., and Baichwal, V. R., Adv. Immunol., 65:111-136, 1997). Although the majority of NF-κB activators result in IκB phosphorylation, it is clear that multiple pathways lead to this key event. Receptor-mediated NF-κB activation relies upon specific interactions between the receptor and adapter/signaling molecules (for example, TRADD, RIP, TRAF, MyD88) and associated kinases (IRAK, NIK) (Song et. al., Proc. Natl. Acad. Sci. USA 94:9792-9796, 1997; Natoli et. al., JBC 272:26079-26082, 1997). Environmental stresses such as UV light and γ-radiation appear to stimulate NF-κB via alternative, less defined, mechanisms.

Recent publications have partially elucidated the NF-κB activation. This work has identified three key enzymes which regulate specific IκB/NF-κB interactions: NF-κB inducing kinase (NIK) (Boldin et. al., Cell 85:803-815, 1996), IκB kinase-1 (IKK-1) (Didonato et. al., Nature 388:548, 1997; Regnier at. al., Cell 90:373 1997) and IB kinase-2 (IKK-2) (Woronicz et. al., Science 278:866, 1997; Zandi et. al., Cell 91:243, 1997).

NIK appears to represent a common mediator of NF-κB signaling cascades triggered by tumour necrosis factor and interleukin-1, and is a potent inducer of IκB phosphorylation. However NIK is unable to phosphorylate IκB directly.

IKK-1 and IKK-2 are thought to lie immediately downstream of NIK and are capable of directly phosphorylating all three IκB sub-types. IKK-1 and IKK-2 are 52% identical at the amino acid level but appear to have similar substrate specificities; however, enzyme activities appear to be different: IKK-2 is several-fold more potent than IKK-1. Expression data, coupled with mutagenesis studies, suggest that IKK-1 and IKK-2 are capable of forming homo- and heterodimers through their C-terminal leucine zipper motifs, with the heterodimeric form being preferred (Mercurio et. al., Mol. Cell Biol., 19:1526, 1999; Zandi et. al., Science; 281: 1360, 1998; Lee et. al, Proc. Natl. Acad. Sci. USA 95:9319, 1998).

NIK, IKK-1 and IKK-2 are all serine/threonine kinases. Recent data has shown that tyrosine kinases also play a role in regulating the activation of NF-κB. A number of groups have shown that TNF-α induced NF-κB activation can be regulated by protein tyrosine phosphatases (PTPs) and tyrosine kinases (Amer et. al., JBC 273:29417-29423, 1998; Hu et. al., JBC 273:33561-33565, 1998; Kaekawa et. al., Biochem. J. 337:179-184, 1999; Singh et. al., JBC 271 31049-31054, 1996). The mechanism of action of these enzymes appears to be in regulating the phosphorylation status of IκB. For example, PTP1B and an unidentified tyrosine kinase appear to directly control the phosphorylation of a lysine residue (K42) on IκB-α, which in turn has a critical influence on the accessibility of the adjacent serine residues as targets for phosphorylation by IKK.

Several groups have shown that IKK-1 and IKK-2 form part of a 'signalosome' structure in association with additional proteins including IKAP (Cohen et. al., Nature 395: 292-296, 1998; Rothwarf et. al., Nature 395:297-300, 1998), MEKK-1, putative MAP kinase phosphatase (Lee et. al., Proc. Natl. Acad. Sci. USA 95:9319-9324, 1998), as well as NIK and IκB. Data is now emerging to suggest that although both IKK-1 and IKK-2 associate with NIK, they are differentially activated, and therefore might represent an important integration point for the spectrum of signals that activate NF-κB. Importantly, MEKK-1 (one of the components of the putative signalosome and a target for UV light, LPS induced signaling molecules and small GTases) has been found to activate IK-2 but not IKK-1. Similarly, NIK phosphorylation of IKK-1 results in a dramatic increase in IKK-1 activity but only a small effect on IKK-2 (for review, see Mercurio, F., and Manning, A. M., Current Opinion in Cell Biology, 11:226-232, 1999).

Inhibition of NF-κB activation is likely to be of broad utility in the treatment of inflammatory disease.

There is accumulating evidence that NF-κB signaling plays a significant role in the development of cancer and metastasis. Abnormal expression of c-Rel, NF-κB2 or IκBα have been described in a number of tumour types and tumour cell lines, and there is now data to show that constitutive NF-κB via IKK-2 takes place in a wide range of tumour cell lines. This activity has been linked to various upstream defects in growth factor signaling such as the establishment of autocrine loops, or the presence of oncogene products e.g.

Ras, AKT, Her2, which are involved in the activation of the IKK complex. Constitutive NF-κB activity is believed to contribute to oncogenesis through activation of a range of anti-apoptotic genes e.g. A1/Bfi-1, IEX-1, XIAP, leading to the suppression of cell death pathways, and transcriptional upregulation of cyclin D1 which promotes cell growth. Other data indicate that this pathway is also likely to be involved in the regulation of cell adhesion and cell surface proteases. This suggests a possible additional role for NF-κB activity in the development of metastasis. Evidence confirming the involvement of NF-κB activity in oncogenesis includes the inhibition of tumour cell growth in vitro and in vivo on expression of a modified form of IκBα (super-repressor IκBα).

In addition to the constitutive NF-κB signaling observed in many tumour types, it has been reported that NF-κB is also activated in response to certain types of chemotherapy. Inhibition of NF-κB activation through expression of the super-repressor form of IκBα in parallel with chemotherapy treatment has been shown to enhance the anti-tumour effect of the chemotherapy in xenograft models. NF-κB activity is therefore also implicated in inducible chemoresistance.

Patent application WO 01/58890 discloses certain thiophene carboxamide derivatives that are useful as IKK-2 inhibitors. We now disclose a further group of thiophene carboxamide derivatives that possess desirable pharmacological activity profiles, in particular, increased beneficial potencies.

DISCLOSURE OF THE INVENTION

According to the present invention, there is provided a compound of formula (I)

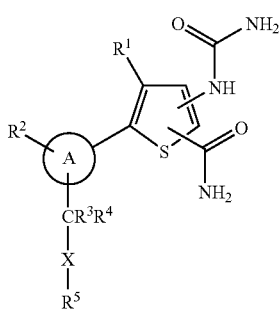

wherein
$R^1$ represents H or $CH_3$;
$R^2$ represents hydrogen, halogen, cyano, C1 to 2 alkyl, trifluoromethyl or C1 to 2 alkoxy;
$R^3$ and $R^4$ independently represent H or $CH_3$; or the group $CR^3R^4$ together represents a C3 to 6 cycloalkyl ring;
A represents a six-membered aromatic ring optionally incorporating one or two nitrogen atoms; and the group —$CR^3R^4$—X—$R^5$ is bonded to ring A in the 4-position relative to the thiophene ring;
X represents $NR^6$;
$R^5$ represents H, C1 to 6 alkyl, C2 to 6 alkenyl or C3 to 6 cycloalkyl; said cycloalkyl group optionally incorporating one heteroatom selected from O, S(O)$_n$ or $NR^7$; said alkyl group being optionally further substituted by one or more groups selected independently from CN, OH, C1 to 4 alkoxy, F, a C5 to 10 monocyclic or bicyclic aromatic ring system optionally incorporating one or two heteroatoms independently selected from O, S and N, and said ring system being optionally further substituted by one or more substituents selected independently from halogen, C1 to 2 alkyl, C1 to 2 alkoxy or $CF_3$; or said alkyl being optionally further substituted by a C5 to 6 cycloalkyl ring that optionally incorporates a heteroatom selected from O, S(O)$_m$ or $NR^8$ and/or a carbonyl group and is optionally further substituted by OH; $R^6$ represents H or C1 to 6 alkyl; said alkyl group being optionally further substituted by CN, OH, Cl to 4 alkoxy or one or more fluoro atoms;
n and m independently represent an integer 0, 1 or 2;
$R^7$ and $R^8$ independently represent H or C1 to 2 alkyl;

and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In one embodiment, $R^1$ in formula (I) represents H.

In another embodiment, $R^2$ in formula (I) represents H.

In another embodiment, A represents an optionally substituted phenyl.

In another embodiment, $R^3$ and $R^4$ in formula (I) each represent H.

In yet another embodiment, $R^5$ represents C1 to 4 alkyl or C3 to 6 cycloalkyl; said cycloalkyl group optionally incorporating one heteroatom selected from O, S(O)$_n$ or $NR^7$; and said alkyl group being optionally further substituted by 1, 2 or 3 groups selected independently from CN, OH, C1 to 4 alkoxy, F, a C5 to 10 monocyclic and bicyclic aromatic ring system optionally incorporating one or two heteroatoms independently selected from O, S and N, and said ring system being optionally further substituted by 1, 2 or 3 substituents selected independently from halogen, C1 to 2 alkyl C1 to 2 alkoxy and $CF_3$; or said alkyl being optionally further substituted by a C5 to 6 cycloalkyl ring that optionally incorporates a heteroatom selected from O, S(O)$_m$ or $NR^8$ and/or a carbonyl group and is optionally further substituted by 1 OH group.

In another embodiment, $R^5$ represents C1 to 6 alkyl or C3 to 6 cycloalkyl; said cycloalkyl group optionally incorporating one heteroatom selected from O, S(O)$_n$ or $NR^7$; and said alkyl group being optionally further substituted by 1, 2 or 3 groups selected independently from CN, OH, C1 to 4 alkoxy, F, a C5 to 10 monocyclic and a bicyclic aromatic ring system optionally incorporating one or two heteroatoms independently selected from O, S and N, and said ring system being optionally further substituted by 1, 2 or 3 substituents selected independently from halogen, C1 to 2 alkyl, C1 to 2 alkoxy and $CF_3$; or said alkyl being optionally further substituted by a C5 to 6 cycloalkyl ring that optionally incorporates a heteroatom selected from O, S(O)$_m$ or $NR^8$ and/or a carbonyl group and is optionally further substituted by 1 OH group.

In another embodiment $R^6$ represents H or C1 to 4 alkyl; said alkyl group being optionally substituted by CN, OH, C1 to 4 alkoxy or by 1, 2 or 3 fluoro atoms.

In one embodiment, the carboxamido group in formula (I) is attached to the 3-position of the thiophene ring.

In another embodiment, the carboxamido group in formula (I) is attached to the 2-position of the thiophene ring.

In one embodiment the present invention relates to a class of compounds of formula (I) wherein $R^1$, $R^2$, $R^3$ and $R^4$ each represent H; the carboxamido group is attached to the 3-position of the thiophene ring; the carboxamido group in formula (I) is attached to the 2-position of the thiophene ring; A represents an optionally substituted phenyl; and $R^5$ and $R^6$ are as defined above.

In another embodiment the present invention relates to a class of compounds of formula (I) wherein $R^1$, $R^2$, $R^3$ and $R^4$ each represent H; the carboxamido group is attached to the 3-position of the thiophene ring; the carboxamido group in formula (I) is attached to the 2-position of the thiophene ring; A represents phenyl; R6 is H or C1 to 4 alkyl; said alkyl group being optionally substituted by CN, OH, C1 to 4 alkoxy or by 1, 2 or 3 fluoro atoms; and $R^5$ has any of the definitions defined above.

In another embodiment the present invention relates to a class of compounds of formula (I) wherein $R^1$, $R^2$, $R^3$ and $R^4$ each represent H; the carboxamido group is attached to the 3-position of the thiophene ring; the carboxamido group in formula (I) is attached to the 2-position of the thiophene ring; A represents phenyl; R6 is H or C1 to 4 alkyl; said alkyl group being optionally substituted by CN, OH, C1 to 4 alkoxy or by 1, 2 or 3 fluoro atoms; and $R^5$ represents C1 to 6 alkyl or C3 to 6 cycloalkyl; said cycloalkyl group optionally incorporating one heteroatom selected from O, $S(O)_n$ or $NR^7$; and said alkyl group being optionally further substituted by 1, 2 or 3 groups selected independently from CN, OH, C1 to 4 alkoxy, F, a C5 to 10 monocyclic and a bicyclic aromatic ring system optionally incorporating one or two heteroatoms independently selected from O, S and N, and said ring system being optionally further substituted by 1, 2 or 3 substituents selected independently from halogen, C1 to 2 alkyl, C1 to 2 alkoxy and $CF_3$; or said alkyl being optionally further substituted by a C5 to 6 cycloalkyl ring that optionally incorporates a heteroatom selected from O, $S(O)_m$ or $NR^8$ and/or a carbonyl group and is optionally further substituted by 1 OH group.

The compounds of formula (I) and their pharmaceutically acceptable salts have the advantage that they are inhibitors of the enzyme IKK-2.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof for use as a medicament.

Another aspect of the invention provides the use of a compound of formula (I) or a pharmaceutically acceptable salt thereof, in the manufacture of a medicament, for the treatment or prophylaxis of diseases or conditions in which inhibition of IKK-2 activity is beneficial.

A more particular aspect of the invention provides the use of a compound of formula (I) or a pharmaceutically acceptable salt thereof, in the manufacture of a medicament, for the treatment or prophylaxis of inflammatory disease.

According to the invention, there is also provided a method of treating, or reducing the risk of, diseases or conditions in which inhibition of IKK-2 activity is beneficial which comprises administering to a person suffering from or at risk of, said disease or condition, a therapeutically effective amount of a compound of formula (I), or a pharmaceutically acceptable salt thereof.

More particularly, there is also provided a method of treating, or reducing the risk of inflammatory disease in a person suffering from or at risk of, said disease, wherein the method comprises administering to the person a therapeutically effective amount of a compound of formula (I) or a pharmaceutically acceptable salt thereof.

Particular compounds of the invention include those exemplified herein:

2-[(aminocarbonyl)amino]-5-(4-{[2,2,2-trifluoroethyl) amino]methyl}phenyl)thiophene-3-carboxamide;
2-[(aminocarbonyl)amino]-5-{4-[(isopropylamino)methyl] phenyl}thiophene-3-carboxamide;
2-[(aminocarbonyl)amino]-5-{4-[(bis-(2-methoxyethyl) amino)methyl]phenyl}thiophene-3-carboxamide;
2-[(aminocarbonyl)amino]-5-{4-[(N-ethyl-N-(2-methoxyethyl)amino)methyl]phenyl}-thiophene-3-carboxamide;
2-[(aminocarbonyl)amino]-5-{4-[dimethylaminomethyl] phenyl}thiophene-3-carboxamide;
2-[(aminocarbonyl)amino]-5-{4-[(N-(2,2,2-trifluoroethyl)-N-(2-methoxyethyl)amino)methyl]phenyl}thiophene-3-carboxamide;
2-[(aminocarbonyl)amino]-5-{4-[(2-methoxyethyl)amino) methyl]phenyl}thiophene-3-carboxamide;
2-[(aminocarbonyl)amino]-5-[4-{[(2-(1H-indol-3-yl)ethyl) amino]methyl}phenyl) thiophene-3-carboxamide;
2-[(aminocarbonyl)amino]-5-[4-{methylaminomethyl}phenyl]thiophene-3-carboxamide;
2-[(aminocarbonyl)amino]-5-[4-{cyclopropylaminomethyl}phenyl]thiophene-3-carboxamide;
2-[(aminocarbonyl)amino]-5-[4-{([(2R)-2-hydroxypropyl] amino)methyl}phenyl]thiophene-3-carboxamide;
2-[(aminocarbonyl)amino]-5-[4-{([(2S)-2-hydroxypropyl] amino)methyl}phenyl]thiophene-3-carboxamide;
2-[(aminocarbonyl)amino]-5-[4-{[(tetrahydrofuran-2-ylmethyl)amino]methyl}phenyl]thiophene-3-carboxamide;
2-[(aminocarbonyl)amino]-5-[4-{[(4-fluorobenzyl)amino] methyl}phenyl]thiophene-3-carboxamide;
2-[(aminocarbonyl)amino]-5-[4-{[(3-{2-oxopyrrolidin-1-yl}propyl)amino]methyl}phenyl]thiophene-3-carboxamide;
2-[(aminocarbonyl)amino]-5-[4-{[(1-naphthylmethyl) amino]methyl}phenyl]thiophene-3-carboxamide;
2-[(aminocarbonyl)amino]-5-[4-{([1-(4-chlorobenzyl)-2-hydroxyethyl]amino)methyl}phenyl]thiophene-3-carboxamide;
2-[(aminocarbonyl)amino]-5-[4-{(cyclopentylamino) methyl}phenyl]thiophene-3-carboxamide;
2-[(aminocarbonyl)amino]-5-[4-{[(pyridin-3-ylmethyl) amino]methyl}phenyl]thiophene-3-carboxamide;
2-[(aminocarbonyl)amino]-5-[4-{[(2-[pyridin-2-yl]ethyl) amino]methyl}phenyl]thiophene-3-carboxamide;
2-[(aminocarbonyl)amino]-5-[4-{[({2-hydroxy-1,1-dimethyl}ethyl)amino]methyl}phenyl]thiophene-3-carboxamide;
2-[(aminocarbonyl)amino]-5-[4-{[({1,2-diphenyl}ethyl) amino]methyl}phenyl]thiophene-3-carboxamide;
2-[(aminocarbonyl)amino]-5-[4-{[({2-methoxy-1-methyl}ethyl)amino]methyl}phenyl]thiophene-3-carboxamide;
2-[(aminocarbonyl)amino]-5-[4-{[({2-hydroxy-1-methyl}ethyl)amino]methyl}phenyl]thiophene-3-carboxamide;
2-[(aminocarbonyl)amino]-5-[4-{[(2-methylbenzyl)amino] methyl}phenyl]thiophene-3-carboxamide;
2-[(aminocarbonyl)amino]-5-[4-{[(3-methoxybenzyl) amino]methyl}phenyl]thiophene-3-carboxamide;
2-[(aminocarbonyl)amino]-5-[4-{[(2-fluorobenzyl)amino] methyl}phenyl]thiophene-3-carboxamide;
2-[(aminocarbonyl)amino]-5-[4-{[(3-fluorobenzyl)amino] methyl}phenyl]thiophene-3-carboxamide;
2-[(aminocarbonyl)amino]-5-[4-{[(4-{phenyl}butyl)amino] methyl}phenyl)thiophene-3-carboxamide;
2-[(aminocarbonyl)amino]-5-[4-{([3-(trifluoromethyl)benzyl]amino)methyl}phenyl]thiophene-3-carboxamide;
2-[(aminocarbonyl)amino]-5-[4-{[(5-cyanopentyl)amino) methyl}phenyl]thiophene-3-carboxamide;
2-[(aminocarbonyl)amino]-5-[4-{({2-methyl}propylamino) methyl}phenyl]thiophene-3-carboxamide;
2-[(aminocarbonyl)amino]-5-[4-{[(4-methoxybenzyl) amino]methyl}phenyl]thiophene-3-carboxamide;
2-[(aminocarbonyl)amino]-5-[4-{[(2-phenylethyl)amino] methyl}phenyl]thiophene-3-carboxamide;
2-[(aminocarbonyl)amino]-5-[4-{[(2-hydroxyethyl)amino] methyl}phenyl]thiophene-3-carboxamide;

2-[(aminocarbonyl)amino]-5-[4-{[({2-methoxy-2-methyl}propyl)amino]methyl}phenyl]thiophene-3-carboxamide;
3-[(aminocarbonyl)amino]-5-[4-{[N-(4-fluorobenzyl)-N-methylamino]methyl}phenyl]thiophene-2-carboxamide;
3-[(aminocarbonyl)amino]-5-[4-{[N-(2-{pyridin-2-yl}ethyl)methylamino]methyl}phenyl]thiophene-2-carboxamide;
3-[(aminocarbonyl)amino]-5-[4-{[N-(pyridin-2-ylmethyl)methylamino]methyl}phenyl]thiophene-2-carboxamide;
3-[(aminocarbonyl)amino]-5-[4-{[N-benzyl-N-methylamino]methyl}phenyl]thiophene-2-carboxamide;
3-[(aminocarbonyl)amino]-5-[4-{[N-(2-methoxyethyl)ethylamino]methyl}phenyl]thiophene-2-carboxamide;
3-[(aminocarbonyl)amino]-5-[4-{[(N-{2-methoxyethyl})methylamino]methyl}phenyl]thiophene-2-carboxamide;
3-[(aminocarbonyl)amino]-5-[4-{[N-benzyl-N-(2-cyanoethyl)amino]methyl}phenyl]thiophene-2-carboxamide;
3-[(aminocarbonyl)amino]-5-[4-{[N-(2-cyanoethyl)-N-methylamino]methyl}phenyl]thiophene-2-carboxamide;
3-[(aminocarbonyl)amino]-5-[4-{[N-isopropyl-N-(2-methoxyethyl)amino]methyl}phenyl]thiophene-2-carboxamide;
3-[(aminocarbonyl)amino]-5-[4-{[(3-methoxybenzyl)amino]methyl}phenyl]thiophene-2-carboxamide;
3-[(aminocarbonyl)amino]-5-[4-{[N-(2-methoxyethyl)-N-(pyridin-2-yl)methylamino]methyl}phenyl]thiophene-2-carboxamide;
3-[(aminocarbonyl)amino]-5-[4-{[N-(3,5-dimethyl-1H-pyrazol-yl)methyl]methylamino]methyl}phenyl]thiophene-2-carboxamide;
3-[(aminocarbonyl)amino]-5-[4-{({N-[3-methylisoxazol-5-yl]methyl}methylamino) methyl}phenyl]thiophene-2-carboxamide;
3-[(aminocarbonyl)amino]-5-[4-{[N-(2-hydroxyethyl)methylamino]methyl}phenyl]thiophene-2-carboxamide;
3-[(aminocarbonyl)amino]-5-[4-{[(2-methoxyethyl)amino]methyl}phenyl]thiophene-2-carboxamide;
3-[(aminocarbonyl)amino]-5-[4-{[N-(1,1-dioxotetrahydro-3-thienyl)methylamino]methyl}phenyl]thiophene-2-carboxamide;
3-[(aminocarbonyl)amino]-5-[4-{[N-benzyl-N-(2-hydroxyethyl)amino]methyl}phenyl]thiophene-2-carboxamide;
3-[(aminocarbonyl)amino]-5-[4-{[(tetrahydrofuran-2-ylmethyl)amino]methyl}phenyl]thiophene-2-carboxamide;
3-[(aminocarbonyl)amino]-5-[4-{[(2-methoxy-2-methyl)propylamino]methyl}phenyl]thiophene-2-carboxamide;
2-[(aminocarbonyl)amino]-5-[4-{[N-(2-methoxyethyl)methylamino]methyl}phenyl]thiophene-3-carboxamide;
2-[(aminocarbonyl)amino]-5-[4-{(N,N-diethylamino)methyl}phenyl]thiophene-3-carboxamide;
2-[(aminocarbonyl)amino]-5-[4-{([N-(2-cyanoethyl)-N-methylamino]methyl}phenyl]thiophene-3-carboxamide;
2-[(aminocarbonyl)amino]-5-[4-{[N-benzyl-N-cyanoethylamino]methyl}phenyl]thiophene-3-carboxamide;
2-[(aminocarbonyl)amino]-5-[4-{[N-(2-hydroxyethyl)-N-methylamino]methyl}phenyl]thiophene-3-carboxamide;
2-[(aminocarbonyl)amino]-5-[4-{([N-benzyl-N-(2-hydroxyethyl)]amino)methyl}phenyl]thiophene-3-carboxamide;
2-[(aminocarbonyl)amino]-5-[4-{(bis-[2-hydroxyethyl]amino)methyl}phenyl]thiophene-3-carboxamide;

and pharmaceutically acceptable salts thereof.

Unless otherwise indicated, the term "C1 to 6 alkyl" referred to herein denotes a straight or branched chain alkyl group having from 1 to 6 carbon atoms. Examples of such groups include methyl, ethyl, n-propyl, i-propyl, n-butyl, i-butyl and t-butyl. The term "C1 to 2 alkyl" is to be interpreted analogously.

Unless otherwise indicated, the term "C2 to 6 alkenyl" referred to herein denotes a straight or branched chain alkyl group having 2 to 6 carbon atoms incorporating at least one carbon-carbon double bond. Examples of such groups include ethenyl and propenyl.

Unless otherwise indicated, the term "C3 to 6 cycloalkyl" referred to herein denotes a 5 saturated carbocyclic ring having from 3 to 6 carbon atoms. Examples of such groups include cyclopropyl, cyclopentyl and cyclohexyl.

Unless otherwise indicated, the term "C1 to 4 alkoxy" referred to herein denotes a straight or branched chain alkoxy group having 1 to 4 carbon atoms. Examples of such groups include methoxy, ethoxy and isopropoxy. The term "C1 to 2 alkoxy" is to be interpreted analogously.

Unless otherwise indicated, the term "halogen" referred to herein denotes fluoro, chloro, bromo and iodo.

Examples of a six-membered aromatic ring optionally incorporating one or two nitrogen atoms include phenyl, pyridine, pyridazine, pyrimidine and pyrazine.

Examples of a C3 to 6 cycloalkyl ring that optionally incorporates one heteroatom selected from O, S(O)$_n$ or NR$^8$ include cyclopropyl, cyclopentyl, cyclohexyl, tetrahydrofuranyl, tetrahydropyranyl, tetrahydrothienyl-1,1-dioxide, pyrrolidinyl, pyrrolidonyl and piperidinyl.

Examples of a C5 to 10 monocyclic or bicyclic aromatic ring system optionally incorporating one or two heteroatoms independently selected from O, S and N include phenyl, pyridyl, naphthyl, indolyl, isoxazolyl and pyrazolyl Examples of a C5 to 6 cycloalkyl ring that optionally incorporates a heteroatom selected from O, S(O)$_m$ or NR$^8$ and/or a carbonyl group include cyclohexyl, tetrahydrofuranyl, tetrahydropyranyl, tetrahydrothienyl 1,1-dioxide, pyrrolidinyl, pyrrolidonyl and piperidinyl.

According to the invention there is also provided a process for the preparation of a compound of formula (I) or a pharmaceutically acceptable salt, enantiomer or racemate thereof which comprises:

(a) reaction of a compound of formula (II):

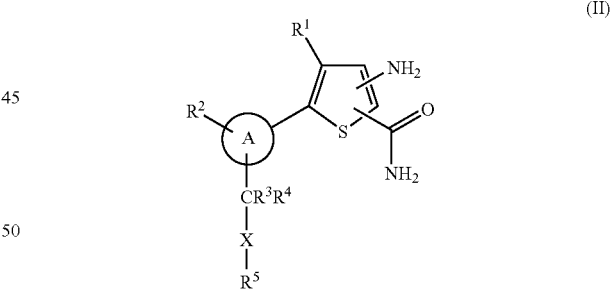

(II)

wherein A, R$^1$, R$^2$, R$^3$, R$^4$, R$^5$ and X are as defined in formula (I) with an isocyanate; or (b) reaction of compound of formula (III)

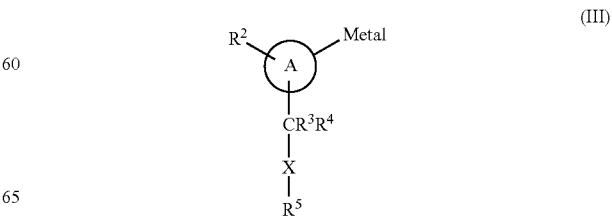

(III)

wherein A, $R^2$, $R^3$, $R^4$, $R^5$ and X are as defined in formula (I), with a compound of formula (IV)

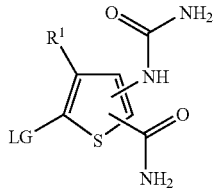

(IV)

wherein $R^1$ is as defined in formula (I) and LG represents a leaving group; or (c) reaction of compound of formula (V)

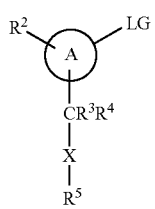

(V)

wherein A, $R^2$, $R^3$, $R^4$, $R^5$ and X are as defined in formula (I) and LG represents a leaving group, with a compound of formula (VI)

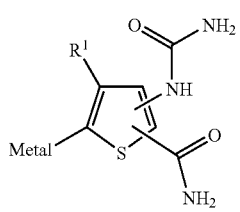

(VI)

wherein $R^1$ is as defined in formula (I); or (d) reaction of compound of formula (VII)

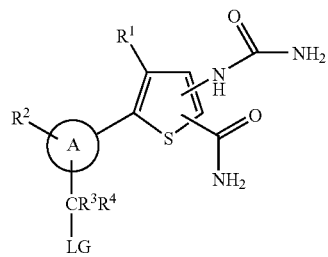

(VII)

wherein A, $R^1$, $R^2$, $R^3$ and $R^4$ are as defined in formula (I), and LG represents a leaving group, with an amine of formula $R^5R^6NH$, wherein $R^5$ and $R^6$ are as defined in formula (I); or (e) reaction of compound of formula (VII)

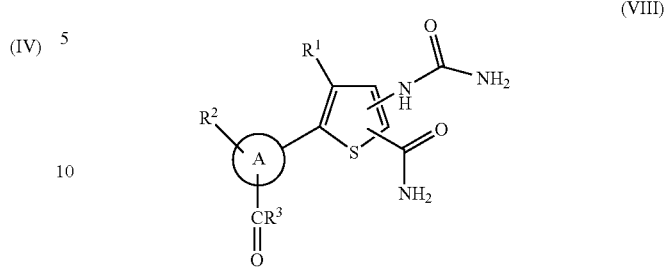

(VIII)

wherein A, $R^1$, $R^2$ and $R^3$ are as defined in formula (I), with an amine of formula $R^5R^6NH$ wherein $R^5$ and $R^6$ are as defined in formula (I), under reductive amination conditions; or (f) reaction of a compound of formula (IX)

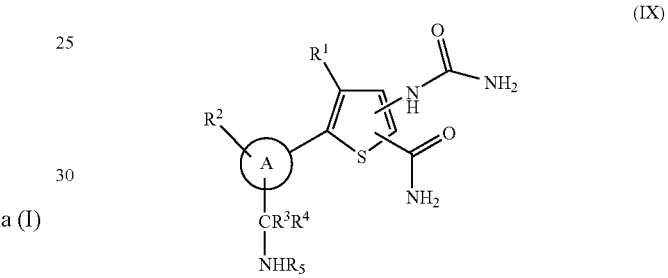

(IX)

wherein $R^1$, $R^2$, $R^3$, $R^4$, $R^5$ and A are as defined in formula (I), with an aldehyde or ketone under reductive amination conditions;

and where necessary converting the resultant compound of formula (I), or another salt thereof into a pharmaceutically acceptable salt thereof; or converting the resultant compound of formula (I) into a further compound of formula (I); and where desired converting the resultant compound of formula (I) into an optical isomer thereof.

In process (a), suitable isocyanate reagents include trimethylsilylisocyanate, trichloroacetylisocyanate and sodium isocyanate. The reaction with trimethylsilylisocyanate can be carried out in a solvent such as dichloromethane/dimethylformamide at a suitable elevated temperature, for example, at the reflux temperature of the reaction mixture. The reaction with sodium isocyanate can be carried out in a suitable solvent system such as aqueous acetic acid at ambient temperature. The trichloroacetylisocyanate reaction can be carried out in a suitable solvent system such as acetonitrile at ambient temperature, and subsequently treating the mixture with ammonia to give compounds of the general formula (I). In a preferred embodiment, the isocyanate is trichloroacetylisocyanate.

In processes (b) and (c), the compounds of formulae (II) and (V) or of formulae (V) and (VI) are reacted together under catalysis provided by a complex of a transition metal such as palladium or nickel. In compounds of formulae (III) and (VI), under appropriate conditions, "metal" can be a metal or semi-metal such as magnesium, zinc, copper, tin, silicon, zirconium, aluminium or boron. Suitable leaving groups include iodo, bromo, chloro, triflate or phosphonate.

In process (d), the compounds of formulae (VII) are reacted together with amines under appropriate reaction conditions. This can either be in the presence or absence of base. Such bases can be either inorganic or organic. Suitable leaving groups include iodo, bromo, chloro, sulphonate and triflate.

In process (e), the carbonyl compounds of formula (VIM) are reacted together with amines under appropriate reductive amination reaction conditions. The reducing agent for these reactions include sodium cyanoborohydride and sodium triacetoxyborohydride. Solvents can include trimethylorthoformate and methanol. Titanium (IV) salts may also be used in this process. Alternatively, compounds of the formula (VIII) can be reacted with amines to form the corresponding imine, which can then be reduced to produce compounds of formula (I). For this route, additional reducing agents such as sodium borohydride may be used.

Conditions for process (f) are analogous to those described above for process (e).

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and removal of one or more protecting groups.

The protection and deprotection of functional groups is described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) can be prepared by standard chemistry described in the literature [for example, J. Heterocyclic Chem., 36, 333 (1999)] or by reaction of compounds of formula (X)

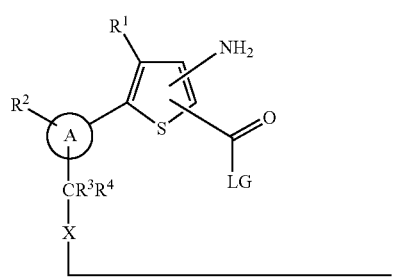

(X)

-continued

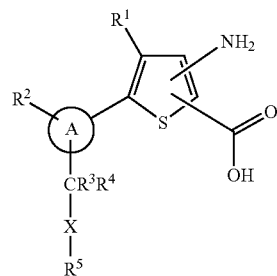

(XI)

where A, $R^1$, $R^2$, $R^3$, $R^4$, $R^5$ and X are as defined in formula (I) with a halogenating agent such as thionyl chloride.

Compounds of formulae (III), (T), (V), (VI), (VII), (VIII) and (IX) are commercially available or can be prepared using standard chemistry as exemplified herein.

Certain novel intermediate compounds form a further aspect of the invention.

The compounds of formula (I) have activity as pharmaceuticals, in particular as IKK-2 enzyme inhibitors, and may be used in the treatment (therapeutic or prophylactic) of conditions/diseases in human and non-human animals in which inhibition of IKK-2 is beneficial. Examples of such conditions/diseases include inflammatory diseases or diseases with an inflammatory component. Particular diseases include inflammatory arthritides including rheumatoid arthritis, osteoarthritis, spondylitis, Reiters syndrome, psoriatic arthritis, lupus and bone resorptive disease; multiple sclerosis, inflammatory bowel disease including Crohn's disease; asthma, chronic obstructive pulmonary disease, emphysema, rhinitis, myasthenia gravis, Graves' disease, allograft rejection, psoriasis, dermatitis, allergic disorders, immune complex diseases, cachexia, ARDS, toxic shock, heart failure, myocardial infarcts, atherosclerosis, reperfusion injury, AIDS, cancer and disorders characterised by insulin resistance such as diabetes, hyperglycemia, hyperinsulinemia, dyslipidemia, obesity, polycystic ovarian disease, hypertension, cardiovascular disease and Syndrome X.

The reported roles of NF-κB in both oncogenesis and chemoresistance suggest that inhibition of this pathway through the use of an IKK-2 inhibitor, such as a small molecule IKK-2 inhibitor, could provide a novel monotherapy for cancer and/or an important adjuvant therapy for the treatment of chemoresistant tumours and in the synergistic induction of apoptosis as a result of combination therapy with an IKK-2 inhibitor with standard therapies or other novel agents.

We are particularly interested in diseases selected from asthma, rheumatoid arthritis, psoriasis, inflammatory bowel disease including Crohn's disease, multiple sclerosis, chronic obstructive pulmonary disease, bone resorptive disease, osteoarthritis, diabetes/glycaemic control and cancer.

Thus, the present invention provides a compound of formula (I), or a pharmaceutically acceptable salt thereof, as hereinbefore defined for use in therapy.

In a further aspect, the present invention provides the use of a compound of formula (I), or a pharmaceutically acceptable salt thereof, as hereinbefore defined in the manufacture of a medicament for use in therapy.

In a still further aspect, the present invention provides the use of a compound of formula (I), or a pharmaceutically acceptable salt thereof, as hereinbefore defined in the manufacture of a medicament for the treatment of diseases or conditions in which modulation of the IKK-2 enzyme activity is beneficial.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating an IKK-2 mediated disease which comprises administering to a patient a therapeutically effective amount of a compound of formula (I), or a pharmaceutically acceptable salt thereof, as hereinbefore defined.

The invention also provides a method of treating an inflammatory disease, especially asthma, rheumatoid arthritis or multiple sclerosis, in a patient suffering from, or at risk of, said disease, which comprises administering to the patient a therapeutically effective amount of a compound of formula (I), or a pharmaceutically acceptable salt thereof, as hereinbefore defined For the above-mentioned therapeutic uses the dosage administered will, of course, vary with the compound employed, the mode of administration, the treatment desired and the disorder indicated.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt thereof, as hereinbefore defined, in association with a pharmaceutically acceptable adjuvant, diluent or carrier.

The invention further provides a process for the preparation of a pharmaceutical composition of the invention, which comprises mixing a compound of formula (I), or a pharmaceutically acceptable salt thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conventional procedures for the selection and preparation of suitable pharmaceutical formulations are described in, for example, "Pharmaceuticals—The Science of Dosage Form Designs", M. E. Aulton, Churchill Livingstone, 1988.

In one aspect of the invention the composition may be adapted for administration by inhalation or insufflation. For example, the composition may be administered in a form suitable for inhalation, for example as a finely divided powder or a liquid aerosol such as an aerosol formed from a predominantly aqueous solution or suspension, or for administration by insufflation, for example as a finely divided powder.

It will be appreciated that delivery by inhalation or insufflation provides higher concentrations of the drug to the required site, namely the epithelial lining of the lungs, than those readily achievable following systemic absorption of the drug. Smaller doses can therefore be used to delivered the drug locally to the specific cells which are to be controlled. Thereby, any adverse systemic side effects of the drug are reduced and the beneficial effects of the treatment can be realised more quickly.

Such administration may use a compressed gas to expel the drug from a container, for example an aerosol formulation may be used comprising fine liquid or solid particles carried by a propellant gas under pressure. The aerosol contains the drug which is dissolved, suspended or emulsified in a mixture of a fluid carrier and a propellant. Conventional propellants may be used, for example hydrocarbons or other suitable gases or mixtures thereof. Conventional metered dose aerosol and breath-activated delivery devices (MDIs) may be employed. Alternatively, the drug may be administered using a conventional nebuliser, which generates fine liquid particles of substantially uniform size containing the drug dispersed as small droplets that can penetrate into the respiratory tract of the patient.

Alternatively, a powder composition containing the drug, with or without a lubricant, carrier or propellant, may be used. For example, a powder mixture of the compound and a suitable powder base such as lactose or starch may be presented in a unit dosage form that may be administered with the aid of an inhaler.

However, certain patients may produce copious quantities of mucus in the lungs and such patients may not be treatable initially by inhalation. In that event, it may be preferable to delivery the pharmaceutical composition of the present invention by injection or orally.

The compositions of the invention may be obtained by conventional procedures using conventional pharmaceutical excipients that are well known in the art. Thus, compositions intended for oral use may contain, for example, one or more colouring, sweetening, flavouring and/or preservative agents.

The invention is illustrated by the following examples: The following abbreviations are used.

DCM Dichloromethane;
DMA N,N-dimethylacetamide;
DME 1,2-Dimethoxyethane;
DMF N,N-Dimethylformamide;
THF Tetrahydrofuran.

Unless otherwise indicated, organic solutions were dried using anhydrous magnesium sulphate.

EXAMPLE 1

2-[(Aminocarbonyl)amino]-5-(4-{[2,2,2-trifluoroethyl)amino]methyl}phenyl)thiophene-3-carboxamide a) N-(4-Bromobenzyl)-N-(2,2,2-trifluoroethyl)amine 4-Bromobenzylbromide (1.5 g) was stirred with 2,2,2-trifluoroethylamine (0.48 ml) and 10 potassium carbonate (0.99 g) in DMA (5 ml) at room temperature for 18 h. The reaction mixture was then poured into water (40 ml) and extracted with ether (3×20 ml). The combined extracts were washed with water, dried, filtered and evaporated. The residue was purified by column chromatography, eluting with a gradient of 3 to 5% ethyl acetate in hexane, to afford the product as a viscous, colourless oil (0.885 g).

MS (ES) 268 (M+H)⁺.

¹H NMR (CDCl₃) 3.15 (q, 2H), 3.87 (s, 2H), 7.20 (d, 2H), 7.46 (d, 2H).

b) 2-[(Aminocarbonyl)amino]-5-(4-{[2,2,2-trifluoroethyl)amino]methyl}phenyl)thiophene-3-carboxamide A mixture of N-(4-bromobenzyl)-N-(2,2,2-trifluoroethyl) amine (0.885 g), bis-(pinacolato)diboron (1.68 g), potassium acetate (0.97 g) and PdCl₂(dppf) (0.097 g) in DMA (15 ml) was flushed with argon, heated at 80° C. for 4 h and then allowed to cool. 2-[(Aminocarbonyl)amino]-5-bromo-3-thiophenecarboxamide (0.349 g) was added, followed by a further portion of PdCl₂(dppf) (0.097 g) and 2M aqueous sodium hydrogen carbonate (4 ml). The mixture was heated at 90° C. for 18 h and allowed to cool to room temperature. The solvent was removed in vacuo and the residue taken up in 2M aqueous sodium hydroxide (50 ml) and DCM (40 ml). The layers were separated and the aqueous layer was washed with further DCM (20 ml). The aqueous phase was filtered to remove a small amount of insoluble material and the filtrate then neutralised with concentrated hydrochloric acid. The precipitated product was collected by filtration and washed with water and dried. The crude material was purified by preparative hplc, product-containing fractions combined, neutralised with concentrated aqueous ammonia and evaporated to give the product as a pale brown solid (0.008 g).

MS (ES) 371 (M−H)⁻.

¹H NMR (DMSO-D6) 2.84-2.95 (m, 1H), 3.11-3.30 (m, 2H), 3.79 (d, 2H), 6.98 (bs, 2H), 7.30 (bs, 1H), 7.36 (d, 2H), 7.50 (d, 2H), 7.67 (bs, 1H), 7.70 (s, 1H), 11.00 (s, 1H).

EXAMPLE 2

2-[(Aminocarbonyl)amino]-5-{4-[(isopropylamino)methyl]phenyl}thiophene-3-carboxamide a) N-[4-(4,4,5,5-Tetramethyl-1,3,2-dioxaborolan-2-yl)benzyl]propan-2-amine Isopropylamine (0.5 ml) was added dropwise to a solution of 2-[4-(bromomethyl)phenyl]-4,4,5,5-tetramethyl-1,3,2-dioxaborolane (0.5 g) in dimethoxymethane (10 ml) and the resulting solution was stirred at room temperature for 18 h. The reaction mixture was evaporated under reduced pressure and used immediately.

b) 2-[(Aminocarbonyl)amino]-5-{4-[(isopropylamino)methyl]phenyl}thiophene-3-carboxamide A solution of N-[4-(4,4,5,5-tetramethyl-1,3,2-dioxaborolan-2-yl)benzyl]propan-2-amine (0.46 g), 2-[(aminocarbonyl)amino]-5-bromothiophene-3-carboxamide (0.2 g) and sodium carbonate (0.32 g) in a DME (15 ml)/water (1.5 ml) mixture was heated to 80° C. under an argon stream. Tetrakis-(triphenylphosphine)palladium(0) (5.1 g) was then added and the reaction was stirred at 90° C. for 4 h, cooled and evaporated under reduced pressure. The residue was partitioned between DCM and saturated sodium carbonate and the solid interlayer was filtered and washed with water. The pure product was obtained by cation exchange chromatography eluting with ammonia/methanol mixtures (0.06 g).

MS (ES) 333 (M+H)⁺.

¹H NMR (DMSO-D6) 1.0 (d, 6H), 2.7 (m, 1H), 3.7 (s, 2H), 6.9 (br, 2H), 7.3 (br, 1H), 7.4 (d, 2H), 7.5 (d, 2H), 7.7 (br, 1H), 7.75 (s, 1H), 11.0 (s, 1H).

EXAMPLE 3

2-[(Aminocarbonyl)amino]-5-{4-[(bis-(2-methoxyethyl)amino)methyl]phenyl}thiophene-3-carboxamide a) N-(4-Bromobenzyl)-2-methoxy-N-(2-methoxyethyl)ethanamide Di-(2-methoxyethyl)amine (6 ml) was added to a solution of 4-bromobenzylbromide (5 g) in DMF (20 ml) at ambient temperature. After stirring at ambient temperature for 2 h, the mixture was partitioned between ethyl acetate and saturated sodium hydrogen carbonate solution. The organic phase was dried, the solvent removed under vacuum to yield a yellow oil which was purified by column chromatography using a 0 to 20% ethyl acetate/isohexane gradient to yield the title compound as a clear oil (4.83 g). MS (M+H)⁺302.

¹H NMR (CDCl₃) 2.72 (t, 4H), 3.3 (s, 6H), 3.45 (t, 4H), 3.64 (s, 2H), 7.21 (d, 2H), 7.41 (d, 2H).

b) 2-[(Aminocarbonyl)amino]-5-{4-[(bis-(2-methoxyethyl)amino)methyl]phenyl}-thiophene-3-carboxamide A solution of N-(4-bromobenzyl)-2-methoxy-N-(2-methoxyethyl)ethanamide (1.6 g) in THF (15 ml) was cooled to −60° C. under argon. Butyl lithium (5 ml, 1.6M solution in hexane) was added dropwise and the mixture was stirred at −60° C. for a further 20 min Triisopropylborate (1.8 ml) was added before allowing the mixture to warm to room temperature. After stirring at room temperature for 3.5 h, the THF was removed under vacuum and DME (20 ml), water (2 ml) and 2-(aminocarbonyl)amino-5-bromo-thiophene-3-carboxamide (0.47 g) were added. The mixture was degassed by purging with argon and sonicating for 15 min, sodium hydrogen carbonate (0.445 g) and Pd(Ph₃)₄ (0.1 g) added and heated to 90° C. for 18 h under argon. The solvent was removed under vacuum and the residue was partitioned between 2N sodium hydroxide solution and DCM. The combined phases were filtered and the aqueous phase was taken to pH 7 by addition of 5N aqueous hydrochloric acid. A precipitate formed which was purified by preparative hplc to yield the product as a solid (0.01 g).

MS (M+H)⁺407.

¹H NMR (DMSO-D6) 2.62 (t, 4H), 3.19 (s, 6H), 3.39 (t, 4H), 3.61 (s, 2H), 6.87-6.95 (bs, 2H), 7.22-7.31 (m, 3H), 7.44 (d, 2H), 7.61-6.9 (m, 2H), 10.97 (s,1H).

EXAMPLE 4

2-[(Aminocarbonyl)amino]-5-{4-[(N-ethyl-N-(2-methoxyethyl)amino)methyl]phenyl}thiophene-3-carboxamide a) The title compound was made from N-(4-bromobenzyl)-N-(2-ethoxyethyl)ethanamine in a similar manner to Example 3 (b) except that it was purified by ion exchange chromatography to yield a cream solid (0.18 g).

MS (M+1)⁺ 377.

¹H NMR (DMSO-D6) 0.97 (t, 3H), 2.48 (q, 2H obscured), 2.57 (t, 2H), 3.2 (s, 3H), 3.39 (t, 2H), 3.55 (s, 2H), 6.91 (bs, 2H), 7.21-7.31 (m, 3H), 7.44 (d, 2H), 7.62-7.69 (m, 2H), 10.97 (bs, 1H).

b) N-(4-Bromobenzyl)-N-(2-methoxyethyl)ethanamine

4-Bromobenzylbromide (4.01 g) was added to a solution of N-(2-ethoxyethyl)ethanamine (3.64 g) in DMF (40 ml). After stirring at ambient temperature for 18 h, the mixture was partitioned between diethyl ether and water. The organic phase was extracted with 2N aqueous hydrochloric acid which was then taken to pH 10 by addition of 2N sodium hydroxide solution. This was then extracted with diethyl ether which was dried and the solvent removed under vacuum to yield the title compound as a yellow oil (4.25 g).

¹H NMR (DMSO-D6) 0.95 (t, 2H), 2.45 (q, 3H), 2.55 (t, 2H), 3.2 (s, 3H), 3.36 (t, 2H), 3.52 (s, 2H), 7.24 (d, 2H), 7.46 (d, 2H).

EXAMPLE 5

2-[(Aminocarbonyl)amino]-5-{4-[dimethylaminomethyl]phenyl}thiophene-3-carboxamide a) The title compound was prepared from 4-(dimethylaminomethyl)phenyl bromide (0.91 g) by the same method as for Example 4 (a) to give the product as a solid (0.155 g).

MS (M+H)⁺ 319.

¹HNMR (DMSO-D6) 2.17 (s, 6H), 3.4 (s, 2H), 7.93 (bs, 2H), 7.21-7.31 (m, 3H), 7.46 (d, 2H), 7.6-7.7 (m, 2H), 10.97 (bs, 1H).

b) 4-(Dimethylaminomethyl)phenyl bromide

2M Ethanolic dimethylamine solution (30 ml) was added to a solution of 4-bromobenzyl bromide (5 g) in DMF (20 ml). The mixture was stirred at ambient temperature for 18 h and was then partitioned between ethyl acetate and saturated aqueous sodium hydrogen carbonate solution. The organic phase was dried, evaporated and purified by column chromatography, eluting with a gradient of 0 to 5% methanol in DCM to yield the product as a clear oil.

MS (M+H)⁺ 214.

¹H NMR (CDCl₃) 2.21 (s, 6H), 3.35 (s, 2H), 7.18 (d, 2H), 7.43 (d, 2H).

EXAMPLE 6

2-[(Aminocarbonyl)amino]-5-{4-[(N-(2,2,2-trifluoroethyl)-N-(2-methoxyethyl)amino)methyl]phenyl}thiophene-3-carboxamide a) The title compound was made in a similar manner to Example 5 (a), but using (4-bromobenzyl)-(2-methoxyethyl)-(2,2,2-trifluoroethyl)amine.

MS(ES) 429 (M−H)⁻.

¹H NMR (DMSO-D6) δ 2.7 (t, 2H), 3.2 (s, 3H), 3.2-3.4 (m, 4H), 3.75 (s, 2H), 6.9 (bs, 2H), 7.2 (bs, 1H), 7.3 (d, 2H), 7.45 (d, 2H), 7.6-7.7 (s+bs, 2H), 10.9 (s, 1H).

b) (4-Bromobenzyl)-(2-methoxyethyl)-(2,2,2-trifluoroethyl)amine

To a solution of 2-bromo-1,1,1-trifluoroethane (0.74 ml) and triethylamine (1.13 ml) in DMF (30 ml) was added (4-bromobenzyl)-(2-methoxyethyl)amine (2.05 g). The resulting mixture was stirred for 18 h. The mixture was partitioned between ethyl acetate and water, the organic layer was dried and evaporated to an oil, which was purified by column chromatography eluting with a gradient of ethyl acetate (60 to 100%) in isohexane to give (4-bromobenzyl)-(2-methoxyethyl)-(2,2,2-trifluoroethyl) amine (1.84 g).

¹H NMR (DMSO-D6) δ 2.1 (bs, 2H), 2.6 (t, 2H), 3.2 (s, 3H), 3.4 (t, 2H), 3.65 (d, 2H), 7.25 (d, 2H), 7.45 (d, 2H).

c) (4-Bromobenzyl)-(2-methoxyethyl)amine

2-Methoxyethylamine (16 ml) was added to a solution of 4-bromobenzaldehyde (17.2 g) in THF (150 ml). Glacial acetic acid (5.32 ml) and MgSO₄ (0.5 g) were added and the mixture was stirred for 45 min. Sodium triacetoxyborohydride (29.7 g) was added and the resulting mixture was stirred for 4 h. The mixture was partitioned between ethyl acetate and saturated sodium bicarbonate. The organic layer was dried and concentrated to an oil, which was purified by column chromatography, eluting with a gradient of ethyl acetate (10 to 100%) in isohexane, then eluting with methanol/DCM (10:90) to give (4-bromobenzyl)-(2-methoxyethyl)amine (13.0 g) as a yellow oil.

MS (ES) 244 (M+H)⁺.

¹H NMR (DMSO-D6) δ 2.05 (bs, 1H), 2.6 (t, 2H), 3.38 (t, 2H), 3.2 (s, 3H), 3.62 (s, 2H), 7.25 (d, 2H), 7.45 (d, 2H).

EXAMPLE 7

2-[(Aminocarbonyl)amino]-5-{4-[(2-methoxyethyl)amino)methyl]phenyl}thiophene-3-carboxamide a) 2-[(Aminocarbonyl)amino]-5-[4-formylphenyl]thiophene-3-carboxamide 2-[(Aminocarbonyl)amino]-5-bromothiophene-3-carboxamide (11.75 g) was stirred in DME (500 ml) and saturated aqueous sodium bicarbonate solution (100 ml), and 4-formylphenyl boronic acid (10 g) was added. The flask was flushed with argon and tetrakis-(triphenylphosphine)palladium(0) (5.1 g) was then added. The reaction was stirred at 90° C. for 2 h, then cooled and evaporated under reduced pressure. The residue was treated with DCM (200 ml) and 2N sodium hydroxide solution (100 ml), and stirred for 20 min. The resulting solid was then isolated by filtration and purified by trituration with ethanol (100 ml), giving the product as a pale green solid (5.75 g).

MS (ES) 290 (M+H)⁺.

¹H NMR (DMSO-D6) 7.05 (s, 2H), 7.40 (s, 1H), 7.75 (m, 3H), 7.90 (d, 2H), 8.00 (s, 1H), 9.95 (s, 1H), 11.10 (s, 1H).

b) 2-[(Aminocarbonyl)amino]-5-{4-[(2-methoxyethyl)amino)methyl]phenyl}thiophene-3-carboxamide 2-[(Aminocarbonyl)amino]-5-[4-formylphenyl]thiophene-3-carboxamide (300 mg) was stirred for 18 h in a mixture of methanol (10 ml), (2-methoxyethyl)amine (0.18 ml) and sodium cyanoborohydride (200 mg). 4N Hydrochloric acid was added until the mixture was acid. It was filtered, evaporated to dryness, dissolved in 2N sodium hydroxide (5 ml), filtered and the pH adjusted to 7 with solid potassium carbonate. The resulting solid was filtered off, washed with water, ether and dried to give the product as a fawn solid (180 mg).

MS (ES) 349 (M+H)⁺.

¹H NMR (DMSO-D6) 2.76 (t, 2H), 3.24 (s, 3H), 3.44 (t, 2H), 3.81 (s, 2H), 6.93 (bs, 2H), 7.30 (bs, 1H), 7.36 (d, 2H), 7.48 (d, 2H), 7.66 (bs, 1H), 7.71 (s, 1H), 10.98 (s, 1H).

EXAMPLE 8

2-[(Aminocarbonyl)amino]-5-[4-{[(2-(1H-indol-3-yl)ethyl)amino]methyl}phenyl)-thiophene-3-carboxamide 2-[(Aminocarbonyl)amino]-5-(4-formylphenyl)thiophene-3-carboxamide (0.05 g) was stirred in a mixture of DME (15 ml), methanol (15 ml) and glacial acetic acid (0.1 ml). Tryptamine (0.136 g) was added and the reaction was stirred at 80° C. for 2 h, and then polymer-supported cyanoborohydride (0.115 g) was added. The reaction was stirred at 80° C. for a further 4 h, and then polymer-supported benzaldehyde (1.33 g) was added. The resins were removed by filtration, and the filtrate was then passed through a 10 g SCX column, washing with methanol (100 ml). The product was eluted using 1M methanolic ammonia (50 ml), this solution was then evaporated to dryness under reduced pressure and the residue purified by chromatography on silica, eluting with DCM/methanol (2M $NH_3$) (20:1), to give the product as an yellow powder (0.032 g).

MS (ES) 434 (M+H)+.

$^1$H NMR (DMSO-D6) 3.00 (s, 4H), 3.96 (s, 2H), 6.95-7.18 (m, 4H), 7.10-7.15 (m, 1H), 7.21 (d, 1H), 7.35 (s, 1H), 7.40 (d, 1H), 7.47 (d, 2H), 7.54-7.59 (m, 3H), 7.73 (s, 1H), 7.79 (s, 1H), 11.05 (s, 1H).

The compounds of Examples 9 to 36 were prepared from 2-[(aminocarbonyl)amino]-5-(4-formylphenyl)thiophene-3-carboxamide and the appropriate amine using the general method of Example 8.

EXAMPLE 9

2-[(Aminocarbonyl)amino]-5-[4-{methylaminomethyl}phenyl]thiophene-3-carboxamide

MS (ES) 303 (M–H)−.

$^1$H NMR (DMSO-D6) 2.29 (s, 3H), 3.65 (s, 2H), 6.94 (s, 2H), 7.27 (s, 1H), 7.34 (d, 2H), 7.48 (d, 2H), 7.66 (s, 1H), 7.70 (s, 1H), 11.00 (s, 1H).

EXAMPLE 10

2-[(Aminocarbonyl)amino]-5-[4-{cyclopropylaminomethyl}phenyl]thiophene-3-carboxamide

MS (ES) 329 (M–H)−.

$^1$H NMR (DMSO-D6) 0.23-0.28 (m, 2H), 0.32-0.38 (m, 2H), 2.06 (m, 1H), 3.71 (s, 2H), 6.94 (s, 2H), 7.27 (s, 1H), 7.34 (d, 2H), 7.46 (d, 2H), 7.63-7.73 (m, 2H), 11.00 (s, 1H).

EXAMPLE 11

2-[(Aminocarbonyl)amino]-5-[4-{([2R)-2-hydroxypropyl]amino)methyl}phenyl]thiophene-3-carboxamide

MS (ES) 349 (M+H)+.

$^1$H NMR (DMSO-D6) 1.05 (d, 3H), 2.42 (d, 2H), 3.70 (s, 2H), 4.42 (m, 1H), 6.94 (s, 2H), 7.27 (s, 1H), 7.34 (d, 2H), 7.47 (d, 2H), 7.64-7.71 (m, 2H), 11.00 (s, 1H).

EXAMPLE 12

2-[(Aminocarbonyl)amino]-5-[4-{([(2S)-2-hydroxypropyl]amino)methyl}phenyl]thiophene-3-carboxamide

MS (ES) 349 (M+H)+.

$^1$H NMR (DMSO-D6) 1.05 (d, 3H), 2.42 (d, 2H), 3.70 (s, 2H), 4.42 (m, 1H), 6.94 (s, 2H), 7.27 (s, 1H), 7.34 (d, 2H), 7.47 (d, 2H), 7.64-7.71 (m, 2H), 11.00 (s, 1H).

EXAMPLE 13

2-[(Aminocarbonyl)amino]-5-[4-{[(tetrahydrofuran-2-ylmethyl)amino]methyl}phenyl]thiophene-3-carboxamide

MS (ES) 375 (M+H)+.

$^1$H NMR (DMSO-D6) 1.47-1.58 (m, 1H), 1.74-1.94 (m, 3H), 2.52-2.56 (m, 2H), 3.56-3.63 (m, 1H), 3.68-3.77 (m, 3H), 3.84-3.92 (m, 1H), 6.94 (s, 2H), 7.27 (s, 1H), 7.33 (d, 2H), 7.47 (d, 2H), 7.66 (s, 1H), 7.69 (s, 1H), 11.00 (s, 1H).

EXAMPLE 14

2-[(Aminocarbonyl)amino]-5-[4-{[(4-fluorobenzyl)amino]methyl}phenyl]thiophene-3-carboxamide

MS (ES) 399 (M+H)+.

$^1$H NMR (DMSO-D6) 3.69 (bs, 4H), 6.94 (s, 2H), 7.10-7.14 (m, 2H), 7.28 (s, 1H), 7.34-7.42 (m, 4H), 7.47 (d, 2H), 7.66 (s, 1H), 7.70 (s, 1H), 11.00 (s, 1H).

EXAMPLE 15

2-[(Aminocarbonyl)amino]-5-[4-{[(3-{2-oxopyrrolidin-1-yl}propyl)amino]methyl}phenyl]thiophene-3-carboxamide

MS (ES) 416 (M+H)+.

$^1$H NMR (DMSO-D6) 1.56-1.67 (m, 2H), 1.85-1.95 (m, 2H), 2.19 (t, 2H), 2.45 (2H obscured), 3.21 (t, 2H), 3.30 (2H obscured), 3.68 (s, 2H), 6.94 (s, 2H), 7.28 (s, 1H), 7.33 (d, 2H), 7.47 (d, 2H), 7.67 (s, 1H), 7.70 (s, 1H), 10.99 (s, 1H).

EXAMPLE 16

2-[(Aminocarbonyl)amino]-5-[4-{[(1-naphthylmethyl)amino]methyl}phenyl]thiophene-3-carboxamide

MS (ES) 431 (M+H)+.

$^1$H NMR (DMSO-D6) 3.81 (s, 2H), 4.14 (s, 2H), 6.94 (s, 2H), 7.28 (s, 1H), 7.39-7.57 (m, 8H), 7.69 (s, 1H), 7.71 (s, 1H), 7.83 (d, 1H), 7.90-7.94 (m, 1H), 8.13-8.18 (m, 1H), 10.99 (s, 1H)

EXAMPLE 17

2-[(Aminocarbonyl)amino]-5-[4-{([1-(4-chlorobenzyl)-2-hydroxyethyl]amino)methyl}phenyl]thiophene-3-carboxamide

MS (ES) 459 (M+H)$^+$.

$^1$H NMR (DMSO-D6) 2.66-2.75 (m, 3H), 3.30 (1H obscured), 3.74 (s, 2H), 4.54 (m, 1H), 6.94 (s, 2H), 7.21-7.35 (in 7H), 7.44 (d, 2H), 7.63-7.70 (m, 2H), 10.99 (s, 1H).

EXAMPLE 18

2-[(Aminocarbonyl)amino]-5-[4-{(cyclopentylamino)methyl}phenyl]thiophene-3-carboxamide

MS (ES) 359 (M+H)$^+$.

$^1$H NMR (DMSO-D6) 1.28-1.79 (m, 8H), 3.01 (s, 1H), 3.67 (s, 2H), 6.94 (s, 2H), 7.27 (s, 1H), 7.34 (d, 2H), 7.46 (d, 2H), 7.62-7.73 (m, 2H), 10.99 (s, 1H).

EXAMPLE 19

2-[(Aminocarbonyl)amino]-5-[4-{[(pyridin-3-ylmethyl)amino]methyl}phenyl]thiophene-3-carboxamide

MS (ES) 382 (M+H)$^+$.

$^1$H NMR (DMSO-D6) 3.69 (s, 2H), 3.72 (s, 2H), 6.94 (s, 2H), 7.27 (s, 1H), 7.32-7.40 (m, 3H), 7.48 (d, 2H), 7.67 (s, 1H), 7.70 (s, 1H), 7.77 (d, 1H), 8.45 (d, 1H), 8.54 (s, 1H) 11.00 (s, 1H).

EXAMPLE 20

2-[(Aminocarbonyl)amino]-5-[4{[(2-[pyridin-2-yl]ethyl)amino]methyl}phenyl]thiophene-3-carboxamide

MS (ES) 396 (M+H)$^+$.

$^1$H NMR (DMSO-D6) 2.88-2.92 (m, 4H), 3.76 (s, 2H), 6.94 (s, 2H), 7.17-7.22 (A, 1H), 7.27 (d, 2H), 7.33 (d, 2H), 7.46 (d, 2H), 7.64-7.71 (m, 3H), 8.47 (m, 1H). 11.00 (s, 1H).

EXAMPLE 21

2-[(Aminocarbonyl)amino]-5-[4-{[({2-hydroxy-1,1-dimethyl}ethyl)amino]methyl)}phenyl]thiophene-3-carboxamide

MS (ES) 363 (M+H)$^+$.

$^1$H NMR (DMSO-D6) 1.02 (s, 6H), 3.30 (2H obscured), 3.64 (s, 2H), 6.92 (s, 2H), 7.26 (s, 1H), 7.35 (d, 2H), 7.46 (d, 2H), 7.68 (m, 2H), 11.00 (s, 1H).

EXAMPLE 22

2-[(Aminocarbonyl)amino]-5-[4-{[({1,2-diphenyl}ethyl)amino]methyl}phenyl]thiophene-3-carboxamide

MS (ES) 471M+H)$^+$.

$^1$H NMR (DMSO-D6) 2.78-2.88 (m, 1H), 2.94-3.03 (m, 1H), 3.40 (d, 1H), 3.54 (d, 1H), 3.76-3.85 (m, 1H), 6.94 (s, 2H), 7.04-7.09 (m, 2H), 7.12-7.32 (m, 11H), 7.40 (d, 2H), 7.62-7.70 (m, 2H), 11.00 (s, 1H).

EXAMPLE 23

2-[(Aminocarbonyl)amino]-5-[4-{[({2-methoxy-1-methyl}etyl)amino]methyl}phenyl]thiophene-3-carboxamide

MS (ES) 363 (M+H)$^+$.

$^1$H NMR (DMSO-D6) 0.99 (d, 3H), 2.80 (m, 1H), 3.16-3.27 (m, 5H), 3.65-3.81 (m, 2H), 6.94 (s, 2H), 7.28 (s, 1H), 7.34 (d, 2H), 7.47 (d, 2H) 7.63-7.72 (m, 2H), 11.00 (s, 1H).

EXAMPLE 24

2-[(Aminocarbonyl)amino]-5-[4-{[({2-hydroxy-1-methyl}ethyl)amino]methyl}phenyl]thiophene-3-carboxamide

MS (ES) 349 (M+H)$^+$.

$^1$H NMR (DMSO-D6) 0.96 (d, 3H), 3.30 (2H obscured), 3.64-3.80 (m, 2H), 4.48 (m, 1H), 6.94 (s, 2H), 7.27 (s, 1H), 7.35 (d, 2H), 7.47 (d, 2H), 7.64-7.72 (m, 2H), 11.00 (s, 1H).

EXAMPLE 25

2-[(Aminocarbonyl)amino]-5-[4-1[(2-methylbenzyl)amino]methyl}phenyl]thiophene-3-carboxamide

MS (ES) 395 (M+H)$^+$.

$^1$H NMR (MSO-D6) 2.27 (s, 3H), 3.66 (s, 2H), 3.74 (s, 2H), 6.95 (s, 2H), 7.12-7.17 (m, 3H), 7.28 (s, 1H), 7.31-7.36 (m, 1H), 7.39 (d, 2H), 7.49 (d, 2H), 7.67 (s, 1H), 7.70 (s, 1H), 11.00 (s, 1H).

EXAMPLE 26

2-[(Aminocarbonyl)amino]-5-[4-{[(3-methoxybenzyl)amino]methyl}phenyl]thiophene-3-carboxamide

MS (ES) 411 (M+H)$^+$.

$^1$H NMR (DMSO-D6) 3.67 (s, 4H), 3.75 (s, 3H), 6.77-6.82 (m, 1H), 6.88-6.98 (m, 4H), 7.22 (t, 1H), 7.27 (s, 1H), 7.36 (d, 2H), 7.47 (d, 2H), 7.67 (s, 1H), 7.70 (s, 1H), 11.00 (s, 1H).

EXAMPLE 27

2-[(Aminocarbonyl)amino]-5-[4-{[(2-fluorobenzyl)amino]methyl}pheny]thiophene-3-carboxamide

MS (ES) 399M+H)+.

¹H NMR (DMSO-D6) 3.71 (s, 2H), 3.73 (s, 2H), 6.94 (s, 2H), 7.10-7.22 (m, 2H), 7.24-7.33 (m, 2H), 7.37 (d, 2H), 7.45-7.55 (m, 3H), 7.67 (s, 1H), 7.70 (s, 1H), 11.00 (s, 1H).

EXAMPLE 28

2-[(Aminocarbonyl)amino]-5-[4-{[3-fluorobenzyl)amino]methyl}phenyl]thiophene-3-carboxamide

MS (ES) 399 (M+H)+.

¹H NMR (DMSO-D6) 3.68 (s, 2H), 3.72 (s, 2H), 6.94 (s, 2H), 7.01-7.08 (m, 1H), 7.15-7.23 (m, 2H), 7.28 (s, 1H), 7.32-7.40 (m, 3H), 7.48 (d, 2H), 7.67 (s, 1H), 7.70 (s, 1H), 11.00 (s, 1H).

EXAMPLE 29

2-[(Aminocarbonyl)amino]-5-[4-{[(4-{Phenyl}butyl)amino]methyl}pheynl]thiophene-3-carboxamide

MS (ES) 421 (M−H)−.

¹H NMR (DMSO-D6) 1.38-1.50 (m, 2H), 1.55-1.66 (m, 2H), 2.51 (2H obscured), 2.57 (t, 2H), 3.66 (s, 2H), 6.94 (s, 2H), 7.12-7.21 (m, 3H), 7.23-7.29 (m, 3H), 7.33 (d, 2H), 7.46 (d, 2H), 7.62-7.74 (m, 2H), 11.00 (s, 1H).

EXAMPLE 30

2-[(Aminocarbonyl)amino]-5-[4-([3-(trifluoromethyl)benzyl]amino)methyl}phenyl]thiophene-3-carboxamide

MS (ES) 447 (M−H)−.

¹H NMR (DMSO-D6) 3.69 (s, 2H), 3.79 (s, 2H), 6.95 (s, 2H), 7.28 (s, 1H), 7.36 (d, 2H), 7.48 (d, 2H), 7.53-7.75 (m, 6H), 11.00 (s, 1H).

EXAMPLE 31

2-[(Aminocarbonyl)amino]-5-[4-{[(5-cyanonentyl)amino]methyl}phenyl]thiophene-3-carboxamide

MS (ES) 384 (M−H)−.

¹H NMR (DMSO-D6) 1.34-1.50 (m, 6H), 1.51-1.60 (m, 2H), 2.48 (t, 2H), 3.67 (s, 2H), 6.94 (s, 2H), 7.28 (s, 1H), 7.34 (d, 2H), 7.46 (d, 2H), 7.61-7.73 (m, 2H), 11.00 (s, 1H).

EXAMPLE 32

2-[(Aminocarbonyl)amino]-5-[4-{({2-methyl}propylamino)methyl}phenyl]thiophene-3-carboxamide The product was purified by reverse phase preparative HPLC yielding the trifluoroacetate salt as a white powder (0.055 g).

MS (ES) 347 (M+H)+.

¹H NMR (DMSO-D6) 0.95 (d, 6H), 1.93-2.02 (m, 1H), 2.75-2.82 (m, 2H), 4.14 (s, 2H), 6.99 (s, 2H), 7.33 (s, 1H), 7.52 (d, 2H), 7.60 (d, 2H), 7.68 (s, 1H), 7.81 (s, 1H), 8.7 (s, 2H), 11.0 (s, 1H).

EXAMPLE 33

2-[(Aminocarbonyl)amino]-5-[4-{[(4-methoxybenzyl)amino]methyl}phenyl]thiophene-3-carboxamide

MS (ES) 411 (M+H)+.

¹H NMR (DMSO-D6) 3.65 (bs, 4H), 3.75 (s, 3H), 6.88 (d, 2H), 6.94 (s, 2H), 7.22-7.31 (m, 3H), 7.35 (d, 2H), 7.47 (d, 2H), 7.66 (s, 1H), 7.69 (s,1H), 11.00 (s, 1H).

EXAMPLE 34

2-[(Aminocarbonyl)amino]-5-[4-{[(2-phenylethyl)amino]methyl}phenyl]thiophene-3-carboxamide

MS (ES) 395 M+H)+.

¹H NMR (DMSO-D6) 2.74 (s, 4H), 3.72 (s, 2H), 6.94 (s, 2H), 7.14-7.35 (m, 8H), 7.46 (d, 2H), 7.67 (s, 1H), 7.70 (s, 1H), 11.00 (s, 1H).

EXAMPLE 35

2-[(Aminocarbonyl)amino]-5-[4-{[(2-hydroxyethyl)amino]methyl}phenyl]thiophene-3-carboxamide The product was purified by reverse phase preparative HPLC yielding the trifluoroacetate salt as a white powder.

MS (ES) 335 (M+H)+.

¹H NMR (DMSO-D6) 2.99 (t, 2H), 3.64-3.70 (m, 2H), 4.17 (s, 2H), 5.22 (t, 1H), 6.99 (s, 2H), 7.33 (s, 1H), 7.52 (d, 2H), 7.59 (d, 2H), 7.68 (s, 1H), 7.80 (s, 1H), 8.83 (s, 2H), 11.02 (s, 1H).

EXAMPLE 36

2-[(Aminocarbonyl)amino]-5-[4-{[({2-methoxy-2-methyl}propyl)amino]methyl}phenyl]thiophene-3-carboxamide

MS (ES) 377 (M+H)+.

¹H NMR (DMSO-D6) 1.11 (s, 6H), 2.37-2.48 (m, 2H), 3.07 (s, 3H), 3.72 (s, 2H), 6.97 (s, 2H), 7.26-7.40 (m, 3H), 7.44-7.52 (m, 2H), 7.65-7.76 (m, 2H), 11.00 (s, 1H).

EXAMPLE 37

3-[(Aminocarbonyl)amino]-5-[4-{[N-(4-fluorobenzyl)-N-methylamino]methyl}phenyl]thiophene-2-carboxamide a) 2-Bromothiophene-4-carboxylic acid Prepared according to the method as described in *J. Am. Chem. Soc.*, 1954, 76, 2445.

MS (ES) 205 (M−H)−.

¹H NMR (DMSO-D6) 7.45 (s, 1H), 8.22 (s, 1H), 12.94 (bs, 1H).

b) 2-Bromo-4 (N-t-butyloxycarbonyl)aminothiophene

2-Bromothiophene-4-carboxylic acid (3 g) was dissolved in dry warm t-butanol (24 ml). Triethylamine (2.02 ml) was added followed by diphenylphosphoryl azide (3.12 ml). The solution was heated slowly to reflux and heating continued at reflux overnight. The reaction mixture was then allowed to cool, poured into water (150 ml) and extracted with ethyl acetate (3×100 ml). The combined extracts were dried, filtered and evaporated. The crude product was purified by column chromatography, eluting with 5% ethyl acetate in hexane, to give a white solid (1.69 g).

MS (ES) 276 (M−H)⁻.

¹H NMR (DMSO-D6) 1.44 (s, 9H), 7.03 (s, 1H), 7.51 (s, 1H), 9.65 (s, 1H).

c) 5-Bromo-3-[(t-but loxycarbonyl)amino]thiophene-2-carboxylic acid

2-Bromo-4-(N-t-butyloxycarbonyl)aminothiophene (1.68 g) was stirred in dry THF (45 ml) under argon and the solution was cooled to −78° C. Lithium diisopropylamide (7.55 ml, 2M solution) was added dropwise and stirring continued for 3.5 h. Powdered $CO_2$ (excess) was added and the mixture stirred for a further 10 minutes before allowing to warm to room temperature. Water (50 ml) was added, the THF was removed in vacuo and the aqueous phase was extracted with ethyl acetate (3×40 ml). The combined extracts were washed with 1M hydrochloric acid (50 ml), water (50 ml) and brine (50 ml), dried, filtered and the solvent evaporated. The residue was triturated with DCM and the product collected by filtration as a pale yellow solid (1.57 g).

MS (ES) 320 (M−H)⁻.

¹H NMR (DMSO-D6) 9.38 (s, 1H), 7.79 (s, 1H), 1.42 (s, 9H).

d) 5-Bromo-3-(t-butyloxycarbonyl)aminothiophene-2-carboxamide

5-Bromo-3-[(t-butyloxycarbonyl)amino]thiophene-2-carboxylic acid (0.80 g) was stirred in acetonitrile (80 ml). Hydroxybenztriazole (1.41 g) and 1-(3-dimethylaminopropyl)-3-ethylcarbodiimide hydrochloride (2.62 g) were added and stirring continued at room temperature for 10 min. Concentrated aqueous ammonia solution (8 ml) was added and the reaction mixture was heated to reflux for 1 h. The acetonitrile was removed by evaporation. Water (100 ml) was added and the mixture was sonicated and triturated. The resultant off-white solid was then collected by filtration, washed with water and dried under vacuum (0.763 g).

MS (ES) 319 (M−H)³¹.

¹H NMR (DMSO-D6) 1.45 (s, 9H), 7.63 (brs, 2H), 7.78 (s, 1H), 10.40 (s, 1H).

e) 3-Amino-5-bromothiophene-2-carboxamide

5-Bromo-3-(t-butyloxycarbonyl)aminothiophene-2-carboxamide (0.76 g) was stirred in DCM (30 ml). Trifluoroacetic acid (5 ml) was added, the solution was stirred at room temperature for 1 h, poured into saturated aqueous sodium hydrogen carbonate solution (200 ml) and extracted with DCM (3×100 ml). The combined extracts were washed with brine (150 ml), dried, filtered and evaporated to give a yellow solid (0.511 g).

MS (ES) 221 (M+H)⁺.

¹H NMR (DMSO-D6) 6.50 (bs, 2H), 6.69 (s, 1H), 6.87 (bs, 2H).

f) 3-[(Aminocarbonyl)amino-5-bromothiophene-2-carboxamide

3-Amino-5-bromothiophene-2-carboxamide (0.25 g) was stirred in anhydrous THF (10 ml), cooled to 0° C. and trichloroacetylisocyanate (0.148 ml) added dropwise. The mixture was allowed to warm to ambient temperature, stirred for 1.5 h and 2M ammonia in methanol (16 ml) added. After 1.5 h, the solvents were evaporated and the residue triturated with diethyl ether and dried in vacuo to give the title compound as a yellow solid (0.26 g).

MS (ES) 264 (M+H)⁺.

¹H NMR (DMSO-D6) 6.63 (bs, 2H), 7.41 (bs, 2H), 7.97 (s, 1H), 10.02 (s, 1H).

g) 3-[(Aminocarbonyl)amino]-5-[4-formylphenyl]thiophene-2-carboxamide

3-[(Aminocarbonyl)amino]-5-bromothiophene-2 carboxamide (2 g) was stirred in DME (200 ml) and saturated aqueous sodium bicarbonate solution (40 ml), and 3-formylphenyl boronic acid (1.7 g) was added. The flask was flushed with argon, and tetrakis-(triphenylphosphine)palladium(0) (0.878 g) was then added The reaction was stirred at 90° C. for 2 h, then cooled and evaporated under reduced pressure. The residue was treated with DCM (200 ml) and saturated aqueous sodium bicarbonate solution (100 ml) and stirred for 20 min. The resulting solid was then isolated by filtration, and purified by sonication in ethanol (100 ml) and the solid isolated by filtration, giving the product as an off white solid (1.53 g).

MS (ES) 288 (M−H)⁻.

¹H NMR (DMSO-D6) 6.68 (s, 2H), 7.52 (s, 2H), 7.67-7.75 (m, 1H), 7.90-7.98 (m, 2H), 8.13 (s, 1H), 8.37 (s, 1H), 10.03-10.12 (m, 2H).

h) 3-[(Aminocarbonyl)amino]-5-[4-{[N-(4-fluorobenzyl)-N-methylamino]methyl}phenyl]thiophene-2-carboxamide The title compound was made from 3-[(aminocarbonyl)amino]-5-[4-formylphenyl]thiophene-2-carboxamide using the general method of Example 8.

MS (ES) 413 (M+H)⁺.

¹H NMR (DMSO-D6) 2.09 (s, 3H), 3.48-3.56 (m, 4H), 6.64 (s, 2H), 7.12-7.21 (m, 2H), 7.34-7.50 (m, 6H), 7.59 (s, 2H), 8.24 (s, 1H), 10.07 (s, 1H).

The compounds of Examples 38 to 55 were prepared from 3-[(aminocarbonyl)amino]-5-(4-formylphenyl) thiophene-2-carboxamide and the appropriate amine using the general method of Example 8.

EXAMPLE 38

3-[(Aminocarbonyl)amino]-5-[4-{[N-(2-{pyridin-2-yl}ethyl)methylamino]methyl}phenyl]thiophene-2-carboxamide

MS (ES) 410 (M+H)⁺.

¹H NMR (DMSO-D6) 2.21 (s, 3H), 2.72 (t, 2H), 2.93 (t, 2H), 3.56 (s, 2H), 6.63 (s, 2H), 7.17-7.22 (m, 1H), 7.26-7.34 (m,

3H), 7.43 (s, 2H), 7.54 (d, 2H), 7.66-7.73 (m, 1H), 8.22 (s, 1H), 8.46 (d, 1H), 10.06 (s, 1H).

EXAMPLE 39

3-[(Aminocarbonyl)amino]-5-[4-{[N-(pyridin-2-ylmethyl)methylamino]methyl}phenyl]thiophene-2-carboxamide

MS (ES) 396 (M+H)$^+$.

$^1$H NMR (DMSO-D6) 2.10 (s, 3H), 3.56 (s, 4H), 6.64 (s, 2H), 7.36-7.50 (m, 5H), 7.60 (d, 2H), 7.77 (d, 1H), 8.24 (s, 1H), 8.45-8.59 (m, 2H), 10.06 (s, 1H).

EXAMPLE 40

3-[(Aminocarbonyl)amino]-5-[4-{[N-benzyl-N-methylamino]methyl}phenyl]thiophene-2-carboxamide

MS (ES) 395 (M+H)$^+$.

$^1$H NMR (DMSO-D6) 2.10 (s, 3H), 3.49-3.57 (m, 4H), 6.60 (s, 2H), 7.22-7.29 (m, 1H), 7.31-7.48 (m, 8H), 7.60 (d, 2H), 8.23 (s, 1H), 10.06 (s, 1H).

EXAMPLE 41

3-[(Aminocarbonyl)amino]-5-[4-{[N-(2-methoxyethyl)ethylamino]methyl}phenyl]thiophene-2-carboxamide

MS (ES) 377 (M+H)$^+$.

$^1$H NMR (DMSO-D6) 0.99 (t, 3H), 2.50 (2H, obscured), 2.61 (t, 2H), 3.23 (s, 3H), 3.43 (t, 2H), 3.62 (s, 2H), 6.60 (s, 2H), 7.34-7.47 (m, 4H), 7.57 (d, 2H), 8.23 (s, 1H), 10.06 (s, 1H).

EXAMPLE 42

3-[(Aminocarbonyl)amino]-5-[4-{[(N-2-methoxyethyl})methylamino]methyl}phenyl]thiophene-2-carboxamide

MS (ES) 363 (M+H)$^+$.

$^1$H NMR (DMSO-D6) 2.18 (s, 3H), 2.53-2.59 (m, 2H), 3.24 (s, 3H), 3.47 (t, 2H), 3.53 (s, 2H), 6.60 (s, 2H), 7.34-7.48 (m, 0.4H), 7.58 (d, 2H), 8.23 (s, 1H), 10.06 (s, 1H).

EXAMPLE 43

3-[(Aminocarbonyl)amino]-5-[4-{[N-benzyl-N-(2-cyanoethyl)amino]methyl}phenyl]thiophene-2-carboxamide

MS (ES) 434 (M+H)$^+$.

$^1$H NMR (DMSO-D6) 2.63-2.77 (m, 4H), 3.60-3.67 (m, 4H), 6.60 (s, 2H), 7.23-7.29 (m, 1H), 7.32-7.46 (m, 6H), 7.48 (d, 2H), 7.60 (d, 2H), 8.23 (s, 1H), 10.06 (s, 1H).

EXAMPLE 44

3-[(Aminocarbonyl)amino]-5-[4-{[N-(2-cyanoethyl)-N-methylamino]methyl}phenyl]thiophene-2-carboxamide

MS (ES) 358 (M+H)$^+$.

$^1$H NMR (DMSO-D6) 2.19 (s, 3H), 2.62-2.74 (m, 4H), 3.57 (s, 2H), 6.59 (s, 2H), 7.35-7.46 (m, 4H), 7.59 (d, 2H), 8.23 (s, 1H), 10.06 (s, 1H).

EXAMPLE 45

3-[(Aminocarbonyl)amino]-5-[4-{[N-isopropyl-N-(2-methoxyethyl)amino]methyl}phenyl]thiophene-2-carboxamide

MS (ES) 391 (M+H)$^+$.

$^1$H NMR (DMSO-D6) 0.99 (d, 6H), 2.57 (t, 2H), 2.85-2.93 (m, 1H), 3.18 (s, 3H), 3.30 (2H obscured), 3.60 (s, 2H), 6.60 (s, 2H), 7.34-7.45 (m, 4H), 7.56 (d, 2H), 8.21 (s, 1H), 10.06 (s, 1H).

EXAMPLE 46

3-[(Aminocarbonyl)amino]-5-[4-{[(3-methoxybenzyl)amino]methyl}phenyl]thiophene-2-carboxamide

MS (ES) 411 (M+H)$^+$.

$^1$H NMR (DMSO-D6) 3.65-3.79 (m, 7H), 6.60 (s, 2H), 6.77-6.83 (m, 1H), 6.89-6.98 (m, 2H), 7.23 (t, 1H), 7.39 (s, 2H), 7.44 (d, 2H), 7.58 (d, 2H), 8.23 (s, 1H), 10.06 (s, 1H).

EXAMPLE 47

3-[(Aminocarbonyl)amino]-5-[4-{[N-(2-methoxyethyl)-N-(pyridin-2-yl) methylamino] methyl}phenyl]thiophene-2-carboxamide

MS (ES) 440 (M+1)$^+$.

$^1$H NMR (DMSO-D6) 2.66 (t, 2H), 3.20 (s, 3H), 3.46 (t, 2H), 3.70 (s, 2H), 3.76 (s, 2H), 6.60 (s, 2H), 7.22-7.28 (m, 1H), 7.39 (s, 2H), 7.43-7.61 (m, 5H), 7.74-7.82 (m, 1H), 8.23 (s, 1H), 8.46-8.51 (m, 1H), 10.06 (s, 1H).

EXAMPLE 48

3-[(Aminocarbonyl)amino]-5-[4-{[N-(3,5-dimethyl-1H-pyrazol-4-yl)methyl]methylamino] methyl}phenyl]thiophene-2-carboxamide

MS (ES) 413 (M+H)$^+$.

$^1$H NMR (DMSO-D6) 2.01 (s, 3H), 2.07-2.16 (m, 6H), 3.23 (s, 2H), 3.44 (s, 2H), 6.60 (s, 2H), 7.33-7.44 (m, 4H), 7.58 (d, 2H), 8.23 (s, 1H), 10.06 (s, 1H).

EXAMPLE 49

3-[(Aminocarbonyl)amino]-5-[4-{({N-[3-methyl-isoxazol-5-yl]methyl]methylamino)methyl}phenyl]thiophene-2-carboxamide

MS (ES) 400 (M+H)+.

$^1$H NMR (DMSO-D6) 2.18 (s, 3H), 2.23 (s, 3H), 3.57 (s, 2H), 3.71 (s, 2H), 6.29 (s, 1H), 6.60 (s, 2H), 7.36-7.47 (m, 4H), 7.60 (d, 2H), 8.24 (s, 1H), 10.06 (s, 1H).

EXAMPLE 50

3-[(Aminocarbonyl)amino]-5-[4-{[N-(2-hydroxy-ethyl)methylamino]methyl}phenyl]thiophene-2-carboxamide

MS (ES) 349. (M+H)+.

$^1$H NMR (DMSO-D6) 2.17 (s, 3H), 2.45 (t, 2H), 3.47-3.57 (m, 4H), 4.34-4.39 (m, 1H), 6.60 (s, 2H), 7.32-7.46 (m, 4H), 7.57 (d, 2H), 8.23 (s, 1H), 10.06 (s, 1H).

EXAMPLE 51

3-[(Aminocarbonyl)amino]-5-[4-{[(2-methoxyethyl)amino]methyl}phenyl]thiophene-2-carboxamide

MS (ES) 349 (M+H)+.

$^1$H NMR (DMSO-D6) 2.69 (t, 2H), 3.25 (s, 3H), 3.42 (t, 2H), 3.77 (s, 2H), 6.60 (s, 2H), 7.34-7.47 (m, 4H), 7.58 (d, 2H), 8.23 (s, 1H), 10.06 (s, 1H).

EXAMPLE 52

3-[(Aminocarbonyl)amino]-5-[4-{[N-(1-dioxidotetrahydro-3-thienyl)methylamino]methyl}phenyl]thiophene-2-carboxamide

MS (ES) 423 (M+H)+.

$^1$H NMR (DMSO-D6) 2.02-2.19 (m, 4H), 2.28-2.39 (m, 1H), 3.01-3.14 (m, 2H), 3.21-3.38 (2H obscured), 3.44-3.69 (m, 3H), 6.60 (s, 2H), 7.33-7.47 (m, 4H), 7.59 (d, 2H), 8.23 (s, 1H), 10.06 (s, 1H).

EXAMPLE 53

3-[(Aminocarbonyl)amino]-5-[4-{[N-benzyl-N-(2-hydroxyethyl)amino]methyl}phenyl]thiophene-2-carboxamide

MS (ES) 425 (M+H)+.

$^1$H NMR (DMSO-D6) 2.57 (t, 2H), 3.43-3.50 (m, 2H), 3.59-3.64 (m, 2H), 3.70 (s, 2H), 4.35-4.40 (m, 1H), 6.60 (s, 2H), 7.27-7.42 (m, 7H), 7.46 (d, 2H), 7.58 (d, 2H), 8.22 (s, 1H), 10.06 (s, 1H).

EXAMPLE 54

3-[(Aminocarbonyl)amino]-5-[4-{[(tetrahydrofuran-2-ylmethyl)amino]methyl}phenyl]thiophene-2-carboxamide

MS (ES) 375 (M+H)+.

$^1$H NMR (DMSO-D6) 1.47-1.59 (m, 1H), 1.73-1.95 (m, 4H), 3.55-3.77 (m, 5H), 3.84-3.94 (m, 1H), 6.60 (s, 2H), 7.34-7.51 (m, 4H), 7.56 (d, 2H), 8.22 (s, 1H), 10.06 (s, 1H).

EXAMPLE 55

K3-[(Aminocarbonyl)amino]-5-[4-{[(2-methoxy-2-methyl)propylamino]methyl}phenyl]thiophene-2-carboxamide

MS (ES) 377 (M+H)+.

$^1$H NMR (DMSO-D6) 1.09 (s, 6H), 2.42 (s, 2H), 3.04 (s, 3H), 3.73 (s, 2H), 6.60 (s, 2H), 7.31-7.44 (m, 4H), 7.54 (d, 2H), 8.19 (s, 1H), 10.03 (s, 1H).

EXAMPLE 56

2-[(Aminocarbonyl)amino]-5-[4-{[N-(2-methoxy-ethyl)methylamino]methyl{phenyl]thiophene-3-carboxamide a) N-(4-Bromobenzyl)-2-methoxy-N-methylethanamine 4-Bromobenzylbromide (1.02 g) and N-(2-methoxyethyl)methylamine (0.73 g) were stirred in DMF (20 ml) for 16 h at ambient temperature. The reaction mixture was then partitioned between diethyl ether (40 ml) and water (40 ml). The aqueous phase was extracted further with diethyl ether (40 ml) and the combined organics were washed with water (50 ml), dried, concentrated in vacuo and purified by column chromatography, eluting with a gradient of ethyl acetate (0 to 50%) in iso-hexane to give the product as a yellow oil (0.67 g).

MS (ES) 258 (M+H)+.

$^1$H NMR (DMSO-D6) 2.10 (s, 3H), 2.45 (m, 2H), 3.20 (s, 3H), 3.40 (m, 4H), 7.21 (m, 2H), 7.45 (m, 2H).

b) The title compound was prepared from N-(4-bromobenzyl)-2-methoxy-N-methylethanamine (0.632 g) and 2-(aminocarbonyl)amino-5-bromo-thiophene-3-carboxamide (0.215 g) in a similar manner to Example 3 (b). The product was obtained directly from the work-up as a brown solid (0.142 g).

MS (ES) 363 (M+H)+.

$^1$H NMR (DMSO-D6) 2.15 (s, 3H), 2.50 (t, 2H), 3.20 (s, 3H), 3.45 (m, 4H), 6.90 (s, 2H), 7.25 (m, 3H), 7.42 (d, 2H), 7.62 (m, 2H), 10.96 (s, 1H).

EXAMPLE 57

2-[(Aminocarbonyl)amino]-5-[4-(N,N-diethylamino)methyl]phenyl}thio hene-3-carboxamide 2-[(Aminocarbonyl)amino]-5-[4-formylphenyl]thiophene-3-carboxamide (0.1 g) was stirred in a mixture of DME (10 ml) and DMA (5 ml). Diethylamine (0.2 ml) was added, followed by trimethyl orthoformate (5 ml) and acetic acid (0.5 ml). The reaction was stirred at 80° C. for 20 min, and then polymer-supported cyanoborohydride (0.45 g) was added. The reaction was stirred at 80° C. for a further 2 h, and then polymer-supported isocyanate (0.5 g) was added. The resins were removed by filtration, and the filtrate passed through a 5 g SCX column, washing with methanol (25 ml). The product was eluted using 1M methanolic ammonia (45 ml), this solution was evaporated to dryness under reduced pressure and the residue purified by chromatography on silica, eluting with DCM/methanol (9:1), to give the product as an off-white solid (0.012 g).

MS (ES) 347 (M+H)+.

$^1$H NMR DMSO-D6) 0.95 (m, 6H), 2.55 (m, 4H), 3.50 (s, 2H), 6.90 (s, 2H), 7.25 (s, 1H), 7.30 (d, 2H), 7.45 (d, 2H), 7.70 (m, 2H), 11.00 (s, 1H).

EXAMPLE 58

2-[(Aminocarbonyl)amino]-5-[4-{([N-(2-cyanoethyl)-N-methylamino]methyl}phenyl]thiophene-3-carboxamide The title compound was prepared using the general method of Example 57.

MS (ES) 358 (M+H)+.

$^1$H NMR (IMSO-D6) 2.20 (s, 3H), 2.60 (m, 2H), 2.75 (m, 2H), 3.55 (s, 2H), 6.90 (s, 2H), 7.30 (s, 11), 7.40 (d, 2H), 7.55 (d, 2H), 7.70 (s, 1H), 7.75 (s, 1H), 11.00 (s, 1H).

EXAMPLE 59

2-[(Aminocarbonyl)amino]-5-[4-{[(N-benzyl-N-cyanoethylamino]methyl}phenyl]thiophene-3-carboxamide The title compound was prepared using the general method of Example 57.

MS (ES) 434 (M+H)+.

$^1$H NMR (DMSO-D6) 2.65 (m, 2H), 2.75 (m, 2H), 3.6 (s, 4H), 6.90 (s, 2H), 7.20-7.35 (m, 6H), 7.40 (d, 2H), 7.55 (d, 2H), 7.65 (s, 1H), 7.75 (s, 1H), 11.00 (s, 1H).

EXAMPLE 60

2-[(Aminocarbonyl)amino]-5-[4-{[N-(2-hydroxyethyl)-N-methylamino]methyl}phenyl]thiophene-3-carboxamide 2-[(Aminocarbonyl)amino]-5-[4-formylphenyl]thiophene-3-carboxamide (0.1 g) was stirred in a mixture of DME (10 ml) and DMA(5 ml). 2-(Methylamino)ethanol (0.13 g) was added, followed by trimethyl orthoformate (5 ml) and acetic acid (0.5 ml). The reaction was stirred at 80° C. for 20 min, and then polymer-supported cyanoborohydride (0.45 g) was added. The reaction was stirred at 80° C. for a further 2 h, and then polymer-supported benzaldehyde (0.5 g) was added. The resins were removed by filtration and the filtrate was passed through a 5 g SCX column, washing with methanol (25 ml). The product was eluted using 1M methanolic ammonia (45 ml) and this solution was evaporated to dryness under reduced pressure. Purification by chromatography on silica, eluting with DCM/methanol (9:1), gave the product as an off-white solid (0.072 g).

MS (ES) 349 (M+H)+.

$^1$H NMR (DMSO-D6) 2.15 (s, 3H), 2.45 (m, 2H), 3.50 (m, 4H), 4.35 (t, 1H), 6.90 (s, 2H), 7.25-7.40 (m, 3H), 7.50 (d, 2H), 7.70 (s, 1H), 7.75 (s, 1H), 11.00 (s, 11).

EXAMPLE 61

2-[(Aminocarbonyl)amino]-5-[4-{([N-benzyl-N-(2-hydroxyethyl)]amino)methyl}phenyl]thiophene-3-carboxamide The title compound was prepared using the general method of Example 60.

MS (ES) 425 (M+H)+.

$^1$H NMR (DMSO-D6) 2.45 (m, 2H), 3.50 (m, 2H), 3.60 (m, 4H), 4.40 (t, 1H), 6.90 (s, 2H), 7.20-7.40 (m, 8H), 7.50 (d, 2H), 7.65 (s, 1H), 7.70 (s, 1H), 11.00 (s, 1H).

EXAMPLE 62

2-[(Aminocarbonyl)amino]-5-[4-{(bis-[2-hydroxyethyl]amino)methyl}phenyl]thiophene-3-carboxamide The title compound was prepared using the general method of Example 60.

MS (ES) 379 (M+H)+.

$^1$H NMR (DMSO-D6) 2.55 (1,4H), 3.45 (m, 4H), 3.60 (s, 2H), 4.35 (m, 2H), 6.90 (s, 2H), 7.25 (s, 1H), 7.35 (d, 2H), 7.45 (d, 2H), 7.65 (s, 1H), 7.75 (s, 1H), 11.00 (s, 1H).

Pharmacological Evaluation of Compounds

IKK-2 Filter Kinase Assay

Compounds were tested for inhibition of IKK-2 using a filter kinase assay. The test compounds were dissolved to 10 mM in dimethylsulphoxide (DMSO). The compounds were then diluted 1 in 40 in kinase buffer (50 mM Tris, pH 7.4 containing 0.1 mM EGTA, 0.1 mM sodium orthovanadate and 0.1% β-mercaptoethanol). 1 in 3 serial dilutions were made from this solution with 2.5% DMSO in kinase buffer. 20 μl of compound dilution was added to wells of a 96 well plate in duplicate. 20 μl 2.5% DMSO in kinase buffer instead of compound was added to control wells (0% inhibition). 20 μl 0.5 M EDTA was added instead of compound to background wells (100% inhibition).

10 μl of a mixture of magnesium acetate, unlabelled ATP, and $^{33}$P-labelled ATP was added to each well made such that the final concentration was 10 mM magnesium acetate, 1 μM ATP and 0.1 μCi $^{33}$P ATP. 20 μl of a mixture of IKK-2 (0.15 μg/well), 1-53 GST-IκB (0.5 μg/well) and bovine serum albumin (BSA) (8.5 μg/well) was added to each well to start the reaction. The final reaction volume was 50 μl.

The kinase reactions were incubated at 21° C. for 80 minutes and the reaction stopped by precipitating the protein by the addition of an equal volume (50 μl) of 20% trichloroacetic acid (TCA). The precipitate was allowed to form for 10 minutes and then filtered onto a GF/C unifilter 96 well plate. Each filter was washed twice with approximately 1 ml 2% TCA.

The filter plate was dried at 30-40° C. for 60 minutes, 20 μl scintillant was added to each well and the plate sealed and radioactivity counted on a Packard Topcount microplate scintillation counter.

When tested in the above assay, the compounds of Examples 1 to 62 gave $IC_{50}$ values of less than 10 μM indicating that they are expected to show useful therapeutic activity.

IKK-1 Filter Kinase Assay

The selectivity of compounds was assessed by testing them for inhibition of IKK-1 using a filter kinase assay. The assay conditions were identical to the IKK-2 filter kinase assay except that a mixture of IKK-1 (0.25 μg/well) and 1-53 GST IκB (9 μg/well) was added to each well to start the reaction.

Inhibition of LPS-induced TNFα production by PBMCs

The effect of test compounds on nuclear factor kappa B (NFκB) activation in cells was assessed by measuring inhibition of tumour necrosis factor alpha (TNFα) production by human peripheral blood mononuclear cells (PBMCs) stimulated by bacterial lipopolysaccharide (LPS).

Human blood (250 ml), anticoagulated with heparin, was collected from healthy volunteers. Aliquots of blood (25 ml) were layered on 20 ml Lymphoprep (Nycomed) in 50 ml polypropylene centrifuge tubes. The tubes were centrifuged (Sorval RT600B) at 2,500 rpm for 30 minutes. The cloudy layer containing PBMCs was collected with a fine tipped Pasteur pipette, transferred into 8 clean polypropylene centrifuge tubes (approximately 10 ml per tube) and diluted to 50 ml with phosphate-buffered saline (PBS). These tubes were centrifuged at 2,000 rpm for 8 minutes. PBS (10 ml) was added to each cell pellet and the cells were gently re-suspended. The cells were pooled in 4 centrifuge tubes, PBS was added to each tube to make the volume up to 50 ml and the tubes were centrifuged at 1,400 rpm for 8 minutes. The cell pellets were again re-suspended in 10 ml PBS, pooled in 2 centrige tubes, the volume made up to 50 ml with PBS and the tubes centrifuged at 900 rpm for 10 minutes.

The final cell pellets were gently re-suspended in 10 ml tissue culture medium (RPMI containing 1% heat-inactivated human serum, L-glutamine and penicillin and streptomycin), combined into 1 tube and the volume made up to 30 ml with RPMI medium. The cells were counted and the cell suspension was diluted to $2.6 \times 10^6$ cells/ml.

Test compounds were dissolved in DMSO to 10 mM and diluted 1 in 250 (40 μM) with RPMI medium. The compounds were then serially diluted 1 in 3 with 0.4% DMSO in RPMI medium. Aliquots of test compound dilutions (50 μl) were transferred to the wells of a 96-well plate. Control wells contained 0.4% DMSO in RPMI instead of compound.

Aliquots of the cell suspension (100 μl) were added to each well and the plates incubated at 37° C. for 30 minutes. 50 μl of 40 μg/ml LPS (Sigma, LA130) was added to wells to stimulate TNFα production by the cells and the plates were incubated overnight at 37° C. RPMI medium (50 μl) was added to negative control wells instead of LPS. The final incubation volume was 200 μl.

Plates were centrifuged for 4 minutes at 1,200 rpm and supernatants were removed for measurement of TNFα concentration. Viability of the remaining cell pellet was measured using WST-1 reagent (Boehringer Mannheim, 1044807). 100 μl RPMI medium containing 10 μl WST-1 reagent was added to each well and the plates were incubated for 0.5 to 3 h. The absorbance at 450 nm was then measured using a 96-well plate spectrophotometer.

TNFα in the supernatants (freshly harvested or stored frozen at −20° C.) were measured using an enzyme-linked immunosorbant assay (ELISA). The ELISA plate was prepared by coating the wells of a 96 well plate with a sheep anti-human TNFα monoclonal antibody (100 μl of 1 μg/ml antibody diluted in coating buffer; 0.5 M carbonate/bicarbonate buffer, pH 9.6 containing 0.2 g/l sodium azide) and incubating overnight at 4° C. Blank wells were not coated. The wells were washed once with 0.1% BSA in PBS containing 0.05% Tween (PBS/Tween) then incubated for 1 h at room temperature with 1% BSA in coating buffer (200 μl). The wells were then washed 3 times with 0.1% BSA in PBS/Tween.

The samples of supernatant from the PBMC incubation were diluted. 1 in 3 with 1% BSA in PBS/Tween. 100 μl aliquots of these dilutions were added to the ELISA plate. Other wells contained 100 μl TNFα standard (10, 3.3, 1.1, 0.37, 0.12, 0.04, 0.014 and 0 ng/ml). The ELISA plate was incubated at room temperature for 2 h before the wells were washed 3 times with 0.1% BSA in PBS/Tween. A rabbit anti-human TNFα antibody (100 μl of a 2.5 μg/ml solution) was added to each well and the plate incubated at room temperature for 1.5 h. The wells were then washed 3 times with 0.1% BSA in PBS/Tween. Goat anti-rabbit IgG-horse radish peroxidase conjugate (ICN, 674371; 100 μl of a 1 in 10,000 dilution) was added to each well and the plate incubated at room temperature for 1.5 h. The wells were washed 3 times with 0.1% BSA in PBS/Tween.

Peroxidase substrate was prepared by dissolving a 1 mg TMB tablet (Sigma, T-5525) in 100 μl DMSO (100 μl) and adding this and 36 μl UHPO (BDH, 30559; 1 g tablet dissolved in 25 ml distilled water) to 10 ml 0.1M citrate/acetate buffer, pH6. 100 μl substrate was added to each well and the plate incubated in the dark at room temperature for approximately 30 minutes. The reaction was stopped by adding 25 μl 2 M sulphuric acid to each well. The absorbance at 450 nm was measured in a 96 well plater spectrophotometer.

Results

| Compound | Inhibition of IKK-2 $IC_{50}$ (μM) | Activity in PBMC Assay $IC_{50}$ (μM) |
|---|---|---|
| Example 1 | 0.0036 | 0.42 |
| Example 5 | 0.013 | 0.12 |
| Example 56 | 0.066 | 0.45 |
| Example 61 | 0.00056 | 0.34 |
| Example 80, WO 01/58890 | 0.2 | 1.01 |
| Example 82, WO 01/58890 | 0.26 | 1.15 |
| Example 77, WO 01/58890 | 0.32 | 1.47 |

The invention claimed is:

1. A compound of formula (I)

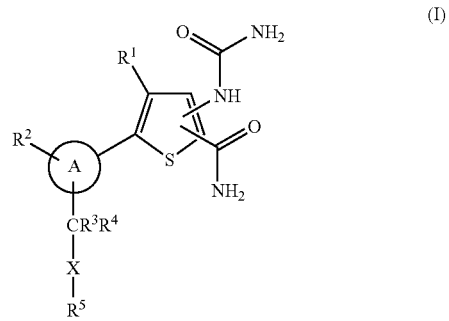

wherein
$R^1$ represents H or $CH_3$;
$R^2$ represents hydrogen, halogen, cyano, C1 to 2 alkyl, trifluoromethyl or C1 to 2 alkoxy;

$R^3$ and $R^4$ independently represent H or $CH_3$;

A represents phenyl; and the group —$CR^3R^4$—X—$R^5$ is bonded to ring A in the 4-position relative to the thiophene ring;

X represents $NR^6$;

$R^5$ represents H, C1 to 6 alkyl, C2 to 6 alkenyl or C3 to 6 cycloalkyl; said alkyl group being optionally further substituted by one or more groups selected independently from CN, OH, C1 to 4 alkoxy, F, a C5 to 10 monocyclic or bicyclic aromatic ring system and said ring system being optionally further substituted by one or more substituents selected independently from halogen, C1 to 2 alkyl, C1 to 2 alkoxy or $CF_3$; or said alkyl being optionally further substituted by a C5 to 6 cycloalkyl ring that optionally incorporates a carbonyl group and is optionally further substituted by OH;

$R^6$ represents H or C1 to 6 alkyl; said alkyl group being optionally further substituted by CN, OH, C1 to 4 alkoxy or one or more fluoro atoms;

n and m independently represent an integer 0, 1 or 2;

$R^7$ and $R^8$ independently represent H or C1 to 2 alkyl;

and pharmaceutically acceptable salts thereof.

2. A compound of formula (I), according to claim 1, wherein $R^1$ represents H.

3. A compound of formula (I), according to claim 1, in which A represents optionally substituted phenyl.

4. A compound of formula (I), according to claim 1, in which $R^3$ and $R^4$ each represent H.

5. A process for the preparation of a compound of formula (I), according to claim 1, which comprises:

(a) reaction of a compound of formula (II):

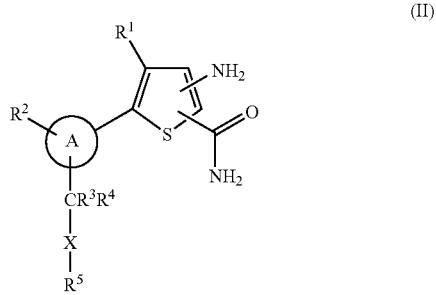

(II)

wherein A, $R^1$, $R^2$, $R^3$, $R^4$, $R^5$ and X are as defined in claim 1 with an isocyanate; or (b) reaction of a compound of formula (III)

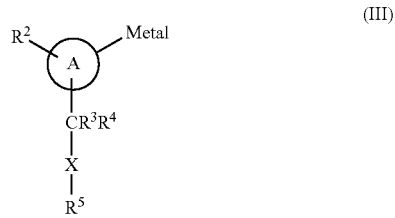

(III)

wherein A, $R^2$, $R^3$, $R^4$, $R^5$ and X are as defined in claim 1, with a compound of formula (IV)

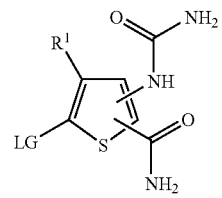

(IV)

wherein $R^1$ is as defined in claim 1 and LG represents a leaving group; or (c) reaction of a compound of formula (V)

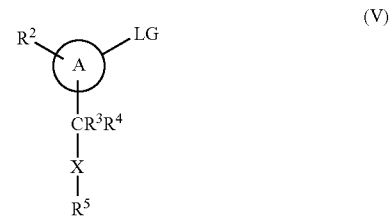

(V)

wherein A, $R^2$, $R^3$, $R^4$, $R^5$ and X are as defined in claim 1 and LG represents a leaving group, with a compound of formula (VI)

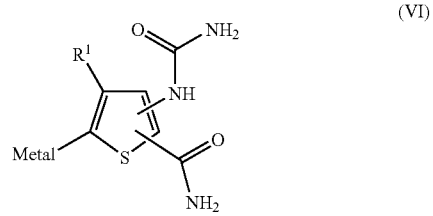

(VI)

wherein $R^1$ is as defined in claim 1; or (d) reaction of a compound of formula (VII)

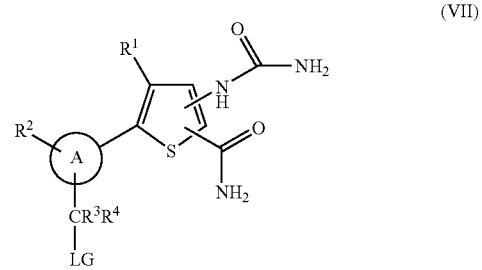

(VII)

wherein A, $R^1$, $R^2$, $R^3$ and $R^4$ are as defined in claim 1, and LG represents a leaving group, with an amine of formula $R^5R^6NH$, wherein $R^5$ and $R^6$ are as defined in claim 1; or (e) reaction of a compound of formula (VIII)

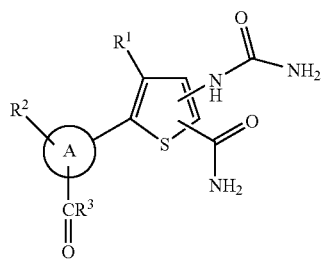

wherein A, $R^1$, $R^2$ and $R^3$ are as defined in claim 1,
with an amine of formula $R^5R^6NH$ wherein $R^5$ and $R^6$ are as defined in claim 1, under reductive amination conditions; or (f) reaction of a compound of formula (IX)

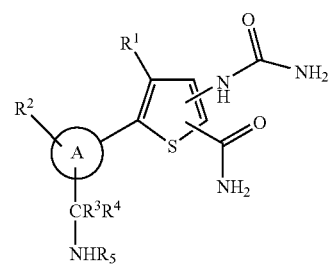

wherein $R^1$, $R^2$, $R^3$, $R^4$, $R^5$ and A are as defined in claim 1, with an aldehyde or ketone under reductive amination conditions;

and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

6. A pharmaceutical composition comprising a compound of formula (I), or a pharmaceutically acceptable salt thereof; as claimed in claim 1 in association with a pharmaceutically acceptable adjuvant, diluent or carrier.

7. A pharmaceutical composition adapted for administration by inhalation or insufflation comprising a compound of formula (I), or a pharmaceutically acceptable salt thereof, as claimed in claim 1 in association with a pharmaceutically acceptable adjuvant, diluent or carrier.

8. A process for the preparation of a pharmaceutical composition which comprises mixing a compound of formula (I), or a pharmaceutically acceptable salt thereof, as claimed claim 1 with a pharmaceutically acceptable adjuvant, diluent or carrier.

9. A method for the treatment or prophylaxis of inflammatory disease selected from the group consisting of asthma, rheumatoid arthritis, psoriasis, inflammatory bowel disease, multiple sclerosis, chronic obstructive pulmonary disease, bone resorptive disease, osteoarthritis, and diabetes/glycemic control, comprising administering to a person suffering from or at risk of said disease a therapeutically effective amount of a compound of formula (I), or a pharmaceutically acceptable salt thereof, as claimed in claim 1.

10. The method as claimed in claim 9 wherein the disease is rheumatoid arthritis.

11. The method as claimed in claim 9 wherein the disease is chronic obstructive pulmonary disease.

12. A method of treating, or reducing the risk of cancer wherein the cancer is selected from the group consisting of colorectal cancer, breast cancer, gastric cancer, Hodgkin's lymphoma, head and neck squamous cell carcinoma, Chronic Myelogenous Leukemia, and Acute Lymphoblastic Leukemia, which comprises administering to a person suffering from or at risk of said disease or condition a therapeutically effective amount of a compound of formula (I), or a pharmaceutically acceptable salt thereof, as claimed in claim 1.

13. A compound of formula (I), according to claim 2, in which A represents optionally substituted phenyl.

14. A compound of formula (I), according to claim 2, in which $R^3$ and $R^4$ each represent H.

15. A compound of formula (I), according to claim 3, in which $R^3$ and $R^4$ each represent H.

16. A compound of formula (I), according to claim 13, in which $R^3$ and $R^4$ each represent H.

* * * * *

UNITED STATES PATENT AND TRADEMARK OFFICE
CERTIFICATE OF CORRECTION

PATENT NO. : 7,572,826 B2  Page 1 of 1
APPLICATION NO. : 10/542326
DATED : August 11, 2009
INVENTOR(S) : Alan Wellington Faull It is certified that error appears in the above-identified patent and that said Letters Patent is hereby corrected as shown below:

Column 37, line 45 (Claim 6), please delete "thereof;" and insert --thereof,-- therefor;

Column 38, line 26 (Claim 12), please delete "cancer" and insert --cancer,-- therefor.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,572,826 B2 | Page 1 of 1 |
| APPLICATION NO. | : 10/542326 | |
| DATED | : August 11, 2009 | |
| INVENTOR(S) | : Faull et al. | |

It is certified that error appears in the above-identified patent and that said Letters Patent is hereby corrected as shown below:

On the cover page,

[*] Notice:   Subject to any disclaimer, the term of this patent is extended or adjusted under 35 U.S.C. 154(b) by 112 days.

Delete the phrase "by 112 days" and insert -- by 172 days --

Signed and Sealed this

Twenty-seventh Day of April, 2010

David J. Kappos
*Director of the United States Patent and Trademark Office*